US008053468B2

(12) United States Patent
Selifonov

(10) Patent No.: US 8,053,468 B2
(45) Date of Patent: Nov. 8, 2011

(54) GLYCEROL LEVULINATE KETALS AND THEIR USE

(75) Inventor: Sergey Selifonov, Plymouth, MN (US)

(73) Assignee: Segetis, Inc., Golden Valley, MN (US)

(*) Notice: Subject to any disclaimer, the term of this patent is extended or adjusted under 35 U.S.C. 154(b) by 449 days.

(21) Appl. No.: 11/915,549

(22) PCT Filed: Nov. 22, 2006

(86) PCT No.: PCT/US2006/045200
§ 371 (c)(1),
(2), (4) Date: May 6, 2008

(87) PCT Pub. No.: WO2007/062118
PCT Pub. Date: May 31, 2007

(65) Prior Publication Data
US 2008/0242721 A1 Oct. 2, 2008

Related U.S. Application Data

(60) Provisional application No. 60/738,988, filed on Nov. 22, 2005.

(51) Int. Cl.
*A61K 31/34* (2006.01)
*C07D 317/22* (2006.01)
(52) U.S. Cl. ........................ 514/467; 549/448
(58) Field of Classification Search .................. 514/467; 549/448
See application file for complete search history.

(56) References Cited

U.S. PATENT DOCUMENTS

| | | | |
|---|---|---|---|
| 1,934,309 A | 11/1933 | Hoover | |
| 2,004,115 A | 6/1935 | Izard | |
| 2,008,720 A | 7/1935 | Lawson | |
| 2,260,261 A | 10/1941 | Morey et al. | |
| 2,556,135 A | 6/1951 | Crozall et al. | |
| 2,654,723 A | 10/1953 | Greene et al. | |
| 2,985,536 A | 5/1961 | Stein et al. | |
| 3,201,420 A | 8/1965 | Fuzesi et al. | |
| 3,658,789 A | 4/1972 | Fried | |
| 4,105,595 A | 8/1978 | Eisenmann et al. | |
| 4,133,800 A | 1/1979 | Taubinger et al. | |
| 4,153,064 A | 5/1979 | Sawada et al. | |
| 4,205,157 A | 5/1980 | Duh | |
| 4,208,527 A | 6/1980 | Horlbeck et al. | |
| 4,460,767 A | 7/1984 | Matsumura et al. | |
| 4,792,411 A | 12/1988 | Walsh | |
| 4,806,448 A | 2/1989 | Roth | |
| 4,897,497 A | 1/1990 | Fitzpatrick | |
| 5,028,667 A | 7/1991 | McLain et al. | |
| 5,095,098 A | 3/1992 | McLain et al. | |
| 5,202,413 A | 4/1993 | Spinu | |
| 5,208,297 A | 5/1993 | Ford et al. | |
| 5,210,108 A | 5/1993 | Spinu et al. | |
| 5,292,859 A | 3/1994 | Ford et al. | |
| 5,342,969 A | 8/1994 | Ford et al. | |
| 5,552,513 A | 9/1996 | Bhatia | |
| 5,565,545 A | 10/1996 | Kriesche et al. | |
| 5,608,105 A | 3/1997 | Fitzpatrick | |
| 5,705,087 A | 1/1998 | Mushrush et al. | |
| 5,741,882 A | 4/1998 | Fujii et al. | |
| 5,859,263 A | 1/1999 | Ghorpade et al. | |
| 5,917,059 A | 6/1999 | Bruchmann et al. | |
| 5,998,092 A | 12/1999 | McCulloch et al. | |
| 6,034,118 A | 3/2000 | Bischofberger et al. | |
| 6,271,279 B1 | 8/2001 | Nodelman et al. | |
| 6,321,465 B1 | 11/2001 | Bonk et al. | |
| 6,395,810 B1 | 5/2002 | Luitjes et al. | |
| 6,528,025 B1 | 3/2003 | Boesch et al. | |
| 6,703,478 B2 | 3/2004 | Nakane et al. | |
| 6,806,392 B2 | 10/2004 | Boesch et al. | |
| 6,828,272 B2 | 12/2004 | Wiegner et al. | |
| 7,153,996 B2 | 12/2006 | Fagan et al. | |
| 2003/0167681 A1 | 9/2003 | Puche | |
| 2004/0010064 A1 | 1/2004 | Harashina et al. | |
| 2004/0024260 A1 | 2/2004 | Winkler et al. | |
| 2004/0167245 A1 | 8/2004 | Chappelow et al. | |
| 2005/0101700 A1 | 5/2005 | Riebel | |
| 2005/0153149 A1 | 7/2005 | Sakane et al. | |
| 2006/0041156 A1 | 2/2006 | Casper et al. | |
| 2006/0069230 A1 | 3/2006 | Papisov | |
| 2006/0211855 A1 | 9/2006 | Doring et al. | |
| 2007/0287645 A1 | 12/2007 | Ollinger et al. | |

FOREIGN PATENT DOCUMENTS

| | | |
|---|---|---|
| CA | 1000285 | 11/1973 |
| DE | 3220035 | 1/1983 |
| DE | 10036423 | 3/2001 |
| EP | 0308956 | 3/1989 |
| EP | 0507190 | 10/1992 |
| FR | 1445013 | 7/1966 |
| JP | 2800437 A | 9/1953 |
| JP | 4217972 | 8/1992 |
| JP | 2006-143702 | 6/2006 |
| SU | 722912 | 3/1980 |
| WO | WO9412489 | 6/1994 |
| WO | WO 96/40609 | 12/1996 |
| WO | WO-2004099173 | 11/2004 |
| WO | WO 2005/070867 A1 | 8/2005 |
| WO | WO 2005/095378 | 10/2005 |
| WO | WO 2005/097723 A2 | 10/2005 |
| WO | WO 2005/097724 A1 | 10/2005 |
| WO | WO 2006/089873 A1 | 8/2006 |
| WO | WO 2007/094922 A2 | 8/2007 |
| WO | WO 2008/089463 A2 | 7/2008 |
| WO | WO 2008/098375 A1 | 8/2008 |

OTHER PUBLICATIONS

Lenz, Robert W., "Structure, Properites, and Cross-linking Reactions of Poly(ester acetals)", Macromolecules, vol. 2, No. 2, Mar.-Apr. 1969, p. 129-136.
Supplementary European Search Report in co-pending EP 06 83 8270, dated Nov. 12, 2009 (9 pages).
Cuiling et al., "Synthesis of Levulinic Ketals with Furfuryl Alcohol as Raw Material", *Journal of Huaqiao University (Nature Science)*, 23(3):257-259 (Jul. 2002) (English Translation).
Gelas et al., "Organic Chemisty. Dihydroxyl Cyclic Acetals Derived from Glycerol", *C.R. Acad. Sc. Paris*, t. 271 (Jul. 20, 1970) Series C, pp. 218-220 (English Translation).

(Continued)

Primary Examiner — Taofiq A Solola
(74) Attorney, Agent, or Firm — Cantor Colburn LLP

(57) ABSTRACT

The present disclosure relates to the preparation of ketal compounds from glycerol and levulinic acid and esters, and uses thereof.

131 Claims, 4 Drawing Sheets

OTHER PUBLICATIONS

Brigl, et al. "The Reaction of the Pyruvic Acid with Glycerin." *Annalen der Chemie* 476; 215-232.

Chou, et al. "A General and Improved Preparation of Monoketals of Symmetrical Diketones with Polymeric Protecting Reagent." *J. Chinese Chem. Soc.* 31; 87-91 (1984).

Grosu, et al. "Stereochemistry and NMR Spectra of Some New Unsymmetrical Substituted 2,2 Dialkyl 1,3 Dioxanes." *Revue Roumaine de Chimie*; 41(3-4); 259-263 (1996).

Gutsche, et al. "Reactions of Ethyl Diazoacetate with Aromatic Compounds Containing Hetero Atoms Attached to the Benzyl Carbon." *J. Am. Chem. Soc.* 76; 2236-2240 (1954).

Hegde, et al. "The Kinetics and Thermodynamics of Bicyclic Ketal Formation: An Application to the Synthesis of the Zaragozic Acids." *Tetrahedron*; 53; 1179-1190 (1997).

Imwinkelried, et al. "Diisopropyl 2,3 O-Isopropylidenetartrate" *Organic Syntheses*; 8; 201-230 (1993).

Lukes, "Preparation of Methyl Esters Containing the 1,3-Dioxane or 2,4,8,10-Tetraoxaspiro[5.5]undecane Structure by Ketal Exchange." *JOC* 26; 2515-2518 (1961).

Meltzer, et al. "2,2-Disubstituted 1,3-Dioxolanes and 2,2-Disubstituted 1,3-Dioxanes." *JOC*; 25; 712 (1960).

Nagata, et al. "Synthesis and Properties [2-methyl 1-2(oxoalkyl)-1,3-dioxolan-4-yl]methyl Methacrylates for Photocrosslinking Agent." *Kobunshi Ronbunshu*; 42 (2); 101-108 (1985)—Japanese.

Nagata, et al. "Synthesis and Applications of 2[2-methyl-2-(oxoalkyl)-1,3-dioxolan-4-yl]methyl Arylates for Photocrosslinking Agent." *Osaka Kogyo Gijutsu Shikensho Kiho*; 37 (1); 8-16 (1986)—Japanese.

Olson, "Subtask 4.1—Conversion of Lignocellulosic Material to Chemicals and Fuels." Final Report for U.S. Dept. of Energy, National Energy Technology Laboratory, Cooperative Agreement No. DE-FC26-98FT40320; Jun. 2001.

Ono, et al. "Synthesis and Properties of Soap Types of Cleavable Surfactants Bearing a 1,3-Dioxolane Ring Derived from Long-chain Epoxides and Ethyl Levulinate." *J. Jpn. Oil Chem. Soc.*; 42 (12) (1993).

Ono, et al. "Preparation, Surface-Active Properties and Acid Decomposition Profiles of a New "Soap" Bearing a 1,3-Dioxolane Ring." *JAOCS*; 70 (1) (1993).

Shevchuk, et al. "Synthesis of Substituted 1,3-Dioxolanes. Part 2. Gas Chromatographic Study of the Reaction of Acetylacetone with Glycerol." *Izvestiya Vysshikh Uchebnykh Zavedenii, Khimiya i Khimicheskaya Tekhnologiya* 42 (5) 14-15 (1999)—Russian.

Stern, et al. "On Hydroboration of 5-Dimethylamino-3-Methyl-1-Pentene and 5-Dimethylamino-3,3-Dimethyl-1-Pentene." *Czechoslov. Chem. Commun.*; 39 (1974).

Takenishi, et al. "The Syntheses from Levulinic Acid. A possible Use of Some 2-Methyl-5-oxopyrrolidine-2-caboxylic Esters as Plasticizers." *Bulletin of the Chemical Society of Japan*, 27 (4); 207-209 (1954).

Xu, et al. "The Use of Polymer Supports in Organic Synthesis. XXVII. The Monoblocking of Symmetrical Diketones on Insoluble Polymer Supports." *Canadian Journal of Chemistry* 61 (7); 1405-1409 (1983).

Yamaguchi, "Synthesis of Polycyclic Aromatic Compounds via Polyketides." *Yuki Gosei Kagaku Kyokaishi* 45 (10) 969-982 (1987)—Chinese.

Yulan, et al. "Synthesis of Ketals of 4-Oxopentanoates." *Lanzhou Daxue Xuebao, Ziran Kexueban* 30(2); 66-70 (1994).

Zhang, et al. "Synthesis of Ketals of 4-Oxopentanoates." *Lanzhou Daxue Zebao, Ziran Kexueban*; (2); 66-70 (1994).

Written Opinion and Search Report from co-pending Singapore Patent Application No. 200803898-6 mailed Feb. 4, 2010 (8 pages).

Anderson et al., "Preparation of carboxylic acids from protected aldehydes." *J. Org. Chem* 43;17(1978): 3417-3418.

Babinsky, R., "PVC additives—A global review." *Journal of Vinyl & Additive Technology* (2007): 1-4.

Bechtold et al., "Perfectly alternating copolymer of lactic acid and ethylene oxide as a plasticizing agent for polyactide." *Macromolecules* 34(2001): 8641-8648.

Biswas et al., "Synthesis of diethylamine-functionalized soybean oil." *J. Agric. Food Chem.* 53(2005): 9485-9490.

Blee et al., "Soybean epoxide hydrolase: Identification of the catalytic residues and probing of the reaction mechanism with secondary kinetic isotope effects." *The Journal of Biological Chemistry* (Dec. 13, 2004): 1-33.

Boehm et al., "Knowledge on cyclic ketals. Part 11: Synthesis of some new derivatives and separation of their isomers." *Pharmazie* 36;5(1981): 329-30.

Bosman et al., "About dendrimers: Structure, physical properties, and applications." *Chem. Rev.* 99(1999): 1665-1688.

Bournay et al., "New heterogeneous process for biodeiesel production: A way to improve the quality and the value of the crude glycerin produced by biodiesel plants." *Catalysis Today* 106(2005): 190-192.

Bozell et al., "Production of levulinic acid and use as a platform chemical for derived products." *Resources, Conservation, and Recycling* 28(2000): 227-229.

Briol et al., "Reaction of pyroacemic acid with glycerol." *Ann.* 476(1929): 215-32.

Brown et al., "Amorphous unsaturated aliphatic polyesters derived from dicarboxylic monomers synthesized by Diels-Alder chemistry." *Marcomolecules* 40(2007): 4848-4853.

Brunelle et al., "Semicrystalline polymers via polymerization of alkylene phthalate cyclic ring-opening polymerization: Preparation and polymerization of alkylene phthalate cyclic oligomers." *Marcomolecules* 31(1998): 4782-4790.

Burch et al., "Synthesis of cyclic oligoesters and their rapid polymerization to high molecular weight." *Marcomolecules* 33(2000): 5053-5064.

Calinaud et al., "Cyclic acetal series. XIII. Opening of 4-oxo and 4-hydroxy-3,6,8-trioxabicyclo[3.2.1]octane and 3-oxo-2,5,7-trioxabicyclo[2.2.2]octane rings by lithium aluminum hydride and methylmagnesium iodide." *Carbohydrate Research* 30;1 (1973). 35-43.

Chang et al., "Levulinic acid production from wheat straw." *Bioresource Technology* 98 (2007). 1448-1453.

Chinn et al., "Polyether polyols for urethanes." *SRI Consulting*. Apr. 2006. Jan. 2008 http://www.sriconsulting.com/CEH/Public/Reports/688.3000/>.

Chirila, T., "Pent-and hexatomic cycloacetal esters. Synthesis and characterization of some 2-carbalkoxymethyl-1,3-dioxolanes (dioxanes)." *Revista de Chimie* 28(1977): 730-733.

Chopade et al., "Acetalization of ethylene glycol with formaldehyde using acation-exchange resins as catalysts: batch versus reactive distillation." *Reactive & Functional Polymers* 34(1997): 37-45.

Clarkson et al., "Continuous reactor technology for ketal formation: An improved synthesis of solketal." *Organic Process Research & Development* 5(2001): 630-635.

Corma et al., "Chemical routes for the transformation of biomass into chemicals." *Chem. Rev.* 107(2007): 2411-2502.

Deutsch et al., "Investigations on heterogeneously catalysed condensations of glycerol to cyclic acetals." *Journal of Catalysis* 245(2007): 428-435.

Di Serio et al., "Transesterification of soybean oil to biodiesel by using heterogeneous basic catalysts." *Ind. Eng. Chem. Res.* 45(2006): 3009-3014.

Edmunds Inc. "New twist on green: 2008 Ford Mustang seats will be soy-based foam." Jul. 12, 2007. Jan. 25, 2008 <http://www.edmunds.com/insideline/do/News/articleId=121682>.

Fowler et al., "The potential industrial uses of forage grasses including miscanthus." *BioComposites Centre*, University of Wales (Jun. 3, 2003): 1-37.

Gelas et al., "Research in the series of the cyclic acetals XII*. Synthesis of the 4-oxo and of 4-hydroxy-3,6,6-trioxasicyclo [3.2.1]Octanes." *Carbohydrate Research* 30;1 (1973): 21-34.

Girisuta et al., "Kinetic study on the acid-catalyzed hydrolysis of cellulose to levulinic acid." *Ind. Eng. Chem. Res.* 46(2007): 1696-1708.

Girisuta et al., "A kinetic study on the conversion of glucose to levulinic acid." *Chemical Engineering research and Design* 84;A5(2006): 339-349.

Gonzalez et al., "Application of fourier transform infrared spectroscopy in the study of interactions between PVC and plasticizers:

PVC/Plasticizer compatibiltiy versus chemical structure of plasticizer." *Journal of Applied Polymer Science* 101(2006): 1731-1737.
Grabarnik et al., "On five-vs six-membered diacetal formation from threitol and the intermediacy of unusually stable protonated species." *J. Org. Chem* 65(2000): 1636-1642.
Hakkarainen, M., "Aliphatic polyesters: Abiotic and biotic degradation and degradation products." *Advances in polymer science* 157(2002): 113-138.
Hall et al., "Synthesis of a series of cyclic oligo (alkylidene isophthalate)s by cyclo-depolymerisation." *Polymer* 41(2000): 1239-1249.
Haskelbhrg et al., "The preparation of glycerol esters of amino acids." *Compt. rend.* (1930): 190270-19072.
Hawker et al., "One-step synthesis of hyperbranched dendritic polyesters." *J. Am. Chem. Soc.* 113(1991): 4583-4588.
Hazimah et al., "Recovery of glycerol and diglycerol from glycerol pitch." *Journal of Oil Palm Research* 15;1(2003): 1-5.
Hense et al., "Direct preparation of diacetals from 1,2-diketones and their use as 1,2-diol protecting groups."*J. Chem. Soc. Perkin Trans.* 1(1997): 2023-2031.
Hibbert et al., "Studies on the reactions relating to carbohydrates and polysaccharides. XVII. Structure of the isometric mthylidene glycerols." *Carbohydrates and Polysaccharides* 50(1928): 3120-3127.
Hill et al., "Studies on the reactions relating to carbohydrates and polysaccharides. XVII. Separation and identification of the iomeric ethylidene glycerols." *Carbohydrates and Polysaccharides* 50(1928): 2242-2249.
Hiltunen et al., "Synthesis and characterization of lactic acid based telechelic prepolymers." *Marcomolecules* 29(1996): 8677-8682.
Hiltunen et al., "Lactic acid based poly (ester-urethanes): Use of hydroxyl terminated prepolymer in urethane synthesis." *Journal of Applied Polymer Science* 8(1998): 1091-1100.
Holland et al., "Analysis of comonomer content and cyclic oligomers of poly(ethylene terephthalate)." *Polymer* 43(2002): 1797-1804.
Hollingsworth, R., "Progress report for the Center of Renewable Resource Chemistries 2007."
Hoydonckx et al., "Esterification and transesterification of renewable chemicals." *Topics in Catalysis* 27; 1-4(2004): 83-96.
Kim et al., "Preparation of high-molecular-weight Poly(L-lactic acid)-based polymers through direct condensation polmerization in bulk state." *Journal of Applied Polymer Science* 100(2006): 466-472.
Kim et al., "Transesterification of vegetable oil to biodiesel using heterogeneous base catalyst." *Catalysis Today* 93-95(2004): 315-320.
Krauskopf, L., "How about alternatives to phthalate plasticizers?." *Jounal of Vinyl & Additive Technology* 9;4(2003): 159-171.
Li et al., "Montmorillonite clay catalysis. Part 2. [1] An efficient and convenient procedure for the preparation of acetals catalysed by montrmorillionite K-10†." *J. Chem. Research (S)* (1997): 26-27.
Lindblad et al., "Polymers from renewable resources." *Advances in polymer science* 157(2002): 139-161.
Lukes, R., "Preparation of methyl esters containing the 1,3-Dioxane or 2,4,8,10-Tetroxaspiro[5.5]undercane structure by ketal exchange." 26 (1961): 2515-2518.
Ma et al., "Biodesiel production: a review." *Bioresource technology* 70(1999): 1-15.
Malmstrom et al., "Hyperbalanced aliphatic polyesters." *Macromolecules* 28(1995): 1698-1703.
Meher et al., "Technical aspects of biodiesel production by transesterification—a review." *RSER* 194(2004): 1-21.
Meltzer et al., "2,2-Disubstituted 1,3-Dioxolanes and 2,2-Disubstituted 1,3-Dioxanes." 25(May 1960): 712-715.
Meskens et al., "Methods for the preparation of acetals from alcohols for oxiranes and carbonyl compounds." *Synethesis* (1981): 501-522.
Miller et al., "Biorenewable fuels and chemicals via reactive distillation." Midtech Midland, May 11, 2006. (Powerpoint Presentation).
Moeini, H., "Preparation and properties of novel green poly(ether-ester urethane)s insulating coatings based on polyols derived from glycolyzed PET, castor oil, and adipic acid and blocked isocyanate." *Journal of Applied Polymer Science* 106(2007): 1853-1859.
Moncrieff, R.W., "Ketals." *The Journal of the American Oil Chemist's Society* (Aug. 1947): 259-261.

Nagahata et al., "Solid-phase thermal polymerization of macrocyclic ethylene terephthalate dimer using various transesterification catalysts." *Journal of Polymer Science: Part A: Polymer Chemistry* 38(2000): 3360-3368.
Nakamura et al., "Study on ketalization reaction of poly(vinyl alcohol) by ketones. VII. Kinetic study on acetalization and ketalization reaction of poly(vinyl alcohol)." *Journal of Polymer Science: Part A: Polymer Chemistry* 34(1996): 3319-3328.
Nakamura et al., "Study on ketalization reaction of poly (vinyl alcohol) by ketones. IX. Kinetic study on acetalization and ketalization reaction of 1,3-Butanediol as a model compound for poly (vinyl alcohol)." *Polymer Science Part B: Polymer Physice* 35;9(2000): 1719-1731.
Newman et al., "Kinetic and equilibrium studies of cyclic ketal formation and hydrolysis." *The Journal of the American Oil Chemist's Society* 80(1958): 6350-6355.
Olson, E., "Subtask 4.1—Conversion of lignocellulosic material to chemicals and fuels." *Energy & Environmental Research Center*, UND. (Jun. 2001).
Ono et al., "Biodegradation of different carboxylate types of cleavable surfactants bearing a 1,3-dioxolane ring." *JAOCS* 72;7(1995): 853-856.
Ono et al., "Preparation, surface-active properties and acid decomposition profiles of a new "soap" bearing a 1,3-dioxolane ring." *JAOCS* 70;1(1993): 29-36.
Ono et al., "Synthesis and properties of soap types of double-chain cleavable surfactants derived from pyruvate." *Journal of Oleo Science* 53;2(2004): 89-95.
Pang et al., "Review of conventional and novel polymerization processes for polyesters." *Prog. Polym. Sci.* 31(2006): 1009-1037.
Pasto et al., "Neighboring group participation by carbonyl oxygen." *Journal of the American Chemical Society* 87:7(1965): 1515-1521.
Patel et al., "Ketalization of ketones with diols catalyzed by metal(IV) phosphates as solid acid catalysts." *Journal of Molecular Catalysis A: Chemical* 194;1-2(2003): 267-271.
Piantadosi et al., "The preparation of cyclic glycerol acetals by transacetalation." *Journal of the American Chemical Society* 80(1958): 6613-6617.
Sarnacke, P., "Soy beans as polymer building blocks." (Aug. 16, 2007). (Powerpoint Presentation).
Showler et al., "Condensation products of glycerol with aldehydes and ketones. 2-substituted m-dioxan-5-OLS and 1,3-dioxolane-4-methanols." *Chem. Rev.* 67(1967): 427-440.
Smith et al., "The gem-Dialkyl effect. III. Kinetic and equilibrium studies of steroid cyclic ketal formation and hydrolysis." *Journal of the American Chemical Society* 90;5(1968): 1253-1257.
Sodergard et al., "Properties of lactic acid based polymers and their correlation with composition." *Prog. Polym. Sci.* 27(2002): 1123-1163.
Takenishi et al., "The syntheses from levulinic acid. A possible use of some 2-methyl-5-oxopyrrolidine-2-carboxylic esters as plasticizers." *The Syntheses from Levulinic Acid* 27;4(1954): 207-209.
Thompson et al., "Characterization of crude glycerol from biodiesel production from multiple feedstocks." *Applied Engineering in Agriculture* 22;2(2006): 261-265.
Timokhin et al., "Levulinic acid in organic synthesis." *Russian Chemical Reviews* 68;1(1999): 73-84.
Van Horn et al., "Cross-linked and functionalized polyester materials constructed using ketoxime ether linkages." *Soft Matter* 3(2007): 1032-1040.
Verlag, G., "Cargill's BiOH polyols business opens manufacturing site in Brazil." *PU Magazine International* Sep. 26, 2007:12-12.
Vermylen et al., "Study of the thermal evolution of the cyclic-oligomer formation in a cyclic-oligomer-free PET." *Journal of Polymer Science: Part A: Polymer Chemistry* 38(2000): 416-422.
Wang et al., "An efficient procedure for protection of carbonyls catalyzed by sulfamic acid." *Journal of Molecular Catalysis A: Chemical* 233(2005): 121-126.
Wardzinska et al., "Influence of the glycol component in dibenzoate plasticizers on the properties of plasticized PVC films." *Journal of Applied Polymer Science* 97(2005): 822-824.

Wedmid et al., "Long-chain stereomeric 2-alkyl-4-methoxycarbonyl-1,3-dioxolanes in glycerol acetal synthesis." *J. Org. Chem* 42;22(1977): 3624-3626.

Werpy et al., "Top value added chemicals from biomass-vol. I-Results of screening for potential candidates from sugars and synthesis gas." *Biomass* (Aug. 2004): 1-69.

Witczak et al., "Carbohydrate synthons in nattural product synthesis." *ACS Symposium Series* 841(2003): 47-83.

Wood et al., "Cyclic polyesters 1. Preparation by a new synthetic method, using polymer-supportedreagents." *Polymer* 34;14(1993): 3052-3058.

Yang et al., "Investigation of homopolymerization rate of perfluoro-4,5-substituted-2-methylene-1,3-dioxolane derivatives and properties of the polymers." *Journal of Flourine Chemistry* 127(2006): 277-281.

Yang et al., "Synthesis of acetalsand ketals catalyzed by tungstosilicic acid suppored on active carbon." *Journal of Zhejiang University of Science* 6B;5(2005): 373-377.

Yu et al., "Polymer blends and composites from renewable resources." *Prog. Polym. Sci.* 31(2006): 576-602.

Zhang et al., "Qualitative analysis of products formed during the acid catalyzed liquefaction of bagasse in ethylene glycol." *Bioresource technology* 98(2007): 1454-1459.

Bayer MaterialScience, "Plasticizers." 23 pages, Mar. 2001.

BOLTORN Dendritic Polymers. Perstorp, 12 pages (2001).

DuPont Tyzor Organic Titanates Technical Note—Direct Esterification, 3 pages (2001).

DuPont Tyzor Organic Titanates Technical Note—Transesterification, 3 pages (2001).

Girisuta, Buana "Levulinic Acid from Lignocellulosic Biomass," Rijksuniversiteit Groningen, pp. 1-149, Nov. 2007.

GLYCEROL LEVULINATE KETALS AND THEIR USE

CROSS-REFERENCE TO RELATED APPLICATIONS

This application is a National Stage application under 35 U.S.C. §371 to International Application No. PCT/US2006/045200 having an International Filing Date of Nov. 22, 2006, which claims benefit under 35 U.S.C. §119(e) to U.S. Provisional Application No. 60/738,988 filed on Nov. 22, 2005, both of which are incorporated by reference in their entirety herewith.

TECHNICAL FIELD

The present disclosure relates to the preparation of ketal compounds from glycerol and levulinic acid and esters.

BACKGROUND

Many known chemical products such as surfactants, plasticizers, solvents, and polymers are currently manufactured from non-renewable, expensive, petroleum-derived or natural gas-derived feedstock compounds. High raw material costs and uncertainty of future supplies requires the discovery and development of surfactants, plasticizers, solvents, and polymers that can be made from inexpensive renewable biomass-derived feedstocks and by simple chemical methods. Glycerol is an inexpensive renewable compound that is readily available as a by-product of biodiesel production or via fermentation of carbohydrates. Levulinic (4-oxopentanoic) acid is another abundant feedstock that is prepared on an industrial scale by acidic degradation of hexoses and hexose-containing polysaccharides such as cellulose, starch, sucrose, and the like. Chemical products produced from these two materials could fill a need for inexpensive, renewable consumer and industrial products.

SUMMARY

Provided herein are ketal compounds prepared from glycerol and levulinic acid or derivatives thereof. In certain embodiments, such ketal compounds can have the formula:

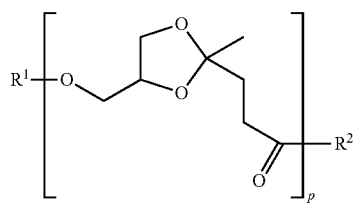

wherein $R^1$ is hydrogen or a carbon atom of a levulinate fragment; $R^2$ is hydroxyl, an oxygen atom of glycerol, or an oxygen atom of an esterified glycerol fragment; and p is an integer. Compounds of this formulation can be prepared through the reaction of glycerol, or a glycerol derivative having the formula:

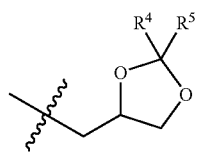

wherein $R^4$ and $R^5$ are independently selected from the group consisting of hydrogen; linear, branched, or cyclic alkyl; linear, branched, or cyclic alkenyl; aryl, and arlyalkyl; and a levulinic acid, levulinic ester, angelicalactone, or a dialkyl ketal of levulinic ester. The reaction can be effected in the presence of an acid catalyst, and under conditions sufficient to provide for removal of water from the reaction mixture.

In another embodiment, a ketal compound can have the formula:

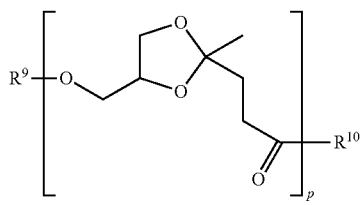

wherein $R^9$ is hydrogen or a carboxyl moiety; $R^{10}$ is $OR^{11}$, or $N(R^{12})_2$; $R^{11}$ and $R^{12}$ are independently hydrogen or a linear, branched, or cyclic alkyl; and p is an integer. This compound can be combined with a monohydric alcohol or carboxylic ester, and a reaction can be effected in the presence of a base catalyst.

An example of a product resulting from such a reaction can include:

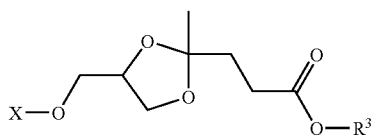

wherein $R^3$ is hydrogen; methyl; linear, branched, or cyclic alkyl; linear, branched, or cyclic alkenyl; aryl, aralkyl, and alkyloxyalkyl; and X is selected from hydrogen or

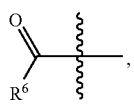

wherein $R^6$ is selected from hydrogen; linear, branched, or cyclic alkyl; linear, branched or cyclic alkenyl; aryl; aralkyl; and alkyloxyalkyl. In some embodiments, it is preferred that $R^3$ is selected from a $C_3$-$C_{30}$ linear, branched, or cyclic alkyl; linear, branched, or cyclic alkenyl; aralkyl; and alkyloxyalkyl. In another embodiment, when $R^3$ is hydrogen, the reaction product can be present as a salt. Suitable salts can include alkali, alkali-earth, ammonia, and amine salts.

In another embodiment, the compound having formula:

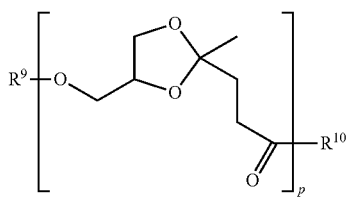

wherein $R^9$ is hydrogen or a carboxyl moiety; $R^{10}$ is $OR^{11}$, or $N(R^{12})_2$; $R^{11}$ and $R^{12}$ are independently hydrogen or a linear, branched, or cyclic alkyl; and p is an integer, can undergo a reaction in the presence of a trans-esterification catalyst. Examples of compounds resulting from such a reaction can include:

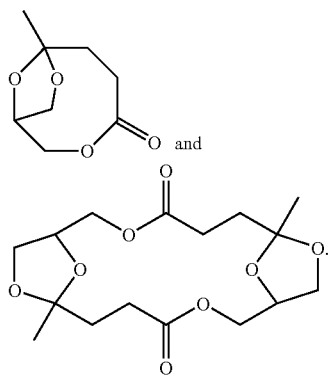

In a further embodiment, compounds can be prepared which have the formula:

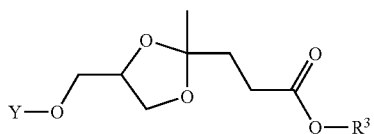

wherein $R^3$ is hydrogen; methyl; linear, branched, or cyclic alkyl; linear, branched, or cyclic alkenyl; aryl, aralkyl, and alkyloxyalkyl; and Y is selected from the group consisting of:

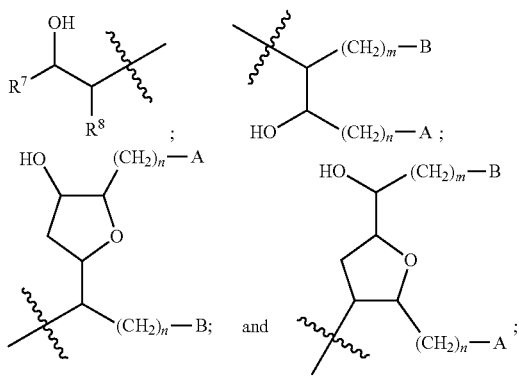

wherein one of $R^7$ or $R^8$ is hydrogen and the other is a $C_1$-$C_{30}$ linear alkyl; one of A or B is hydrogen and the other is an ester; and m and n are independently integers from 0 to 20, wherein the sum of m+n is in the range from 8 to 21. In some embodiments, it is preferred that $R^3$ is selected from $C_3$-$C_{30}$ linear, branched, or cyclic alkyl; linear, branched, or cyclic alkenyl; aralkyl; and alkyloxyalkyl. In another embodiment, $R^7$ or $R^8$ is a $C_6$-$C_{30}$ linear alkyl, or preferably a $C_6$-$C_{14}$ linear alkyl. In certain embodiments, when $R^3$ is hydrogen, the compounds can be present as a salt. Suitable salts can include alkali, alkali-earth, ammonia, and amine salts.

Any of the compounds above can optionally be isolated or prepared in either the cis or trans confirmation. In some cases, the compounds can be predominantly in the cis configuration, i.e., the substituted oxymethylene moiety attached to the dioxolane ring is predominantly in the cis configuration relative to the configuration of the side chain bearing the carboxyl group. Preferably, the compounds are isolated or prepared exclusively in the cis configuration. Alternatively, the compounds can be isolated or prepared in predominantly the trans configuration, i.e., the substituted oxymethylene moiety attached to the dioxolane ring is predominantly in the trans configuration relative to the configuration of the side chain bearing the carboxyl group. As above, the compounds are preferably isolated or prepared exclusively in the trans configuration.

Also provided herein is a polymeric compound comprising a unit having the formula:

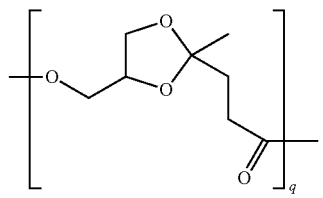

wherein q is an integer.

This polymer, and any of the compounds described above, can be combined with a base polymer to form a plasticized polymer composition. Examples of base polymers can include vinyl chloride polymer, poly(3-hydroxyalkanoate) polymer, poly(lactate) polymer, and polysaccharide polymer.

The details of one or more embodiments of the invention are set forth in the description below. Other features, objects, and advantages of the invention will be apparent from the description and from the claims.

BRIEF DESCRIPTION OF THE DRAWINGS

Referring now to the figures, which are exemplary embodiments.

DETAILED DESCRIPTION

Figure 1:
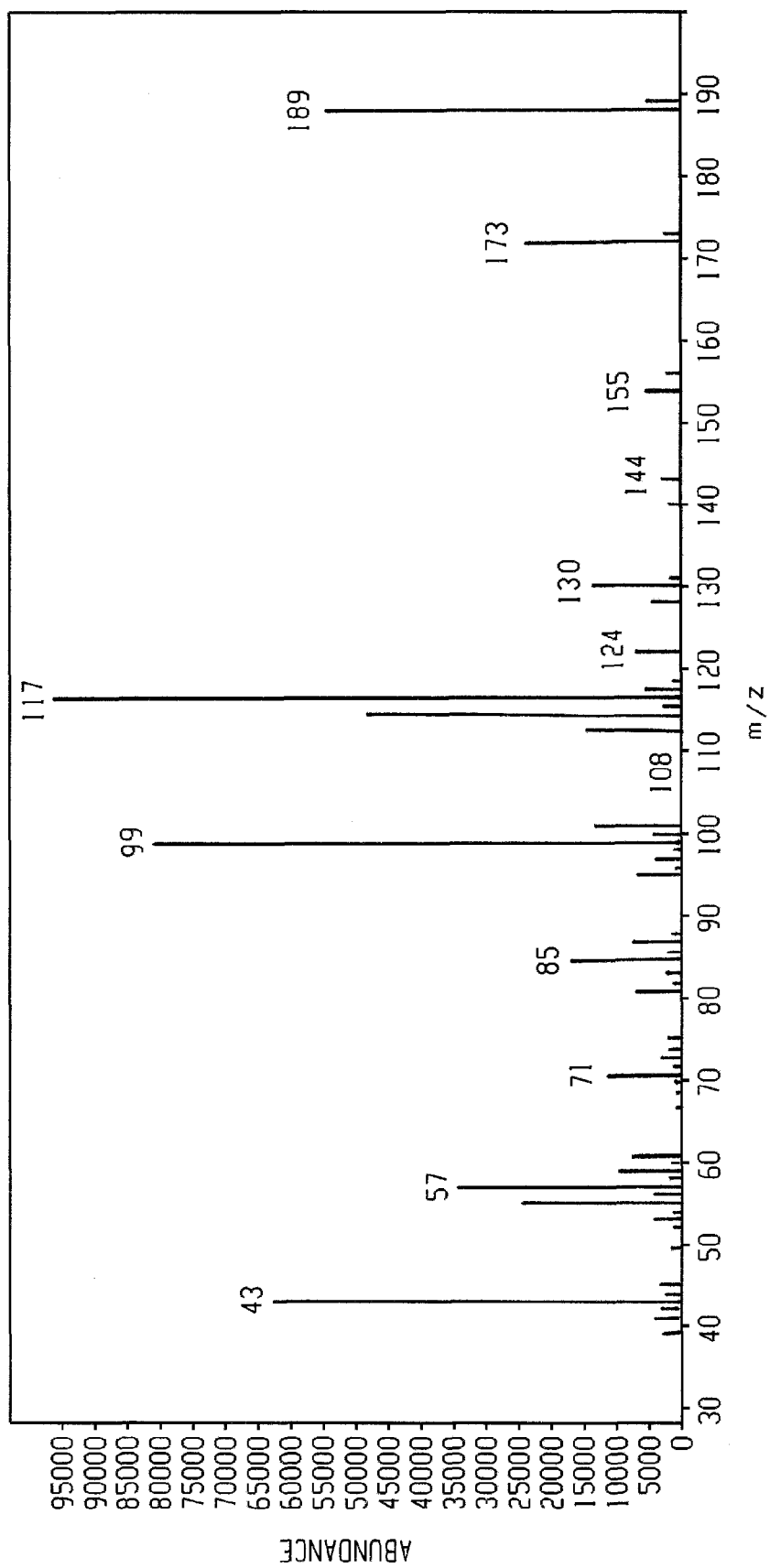
FIG. 1 is a mass spectrum of a stereoisomer prepared according to Example 2.

The present disclosure provides a series of glycerol-derived compounds that are based on the formation of a ketal with the ketone group of levulinic acid. Glycerol-levulinate ketal compounds can be produced by reacting approximately one molar equivalent of glycerol with approximately one molar equivalent of levulinic acid in the presence of an acid catalyst, and under conditions allowing for removal of water, typically by distillation. The reaction is preferably carried out using between 0.7 to 1.3 molar equivalents of levulinic acid, although the reaction can be carried out with lower or higher amounts of levulinic acid. However, when the amount of levulinic acid is too low, much of the glycerol remains unreacted. Alternatively, if the amount of levulinic acid is too high, then di- and tri-levulinate esters of glycerol are formed in large quantities, thereby reducing the yield of the desired ketal adducts of glycerol and levulinate.

During the course of the reaction between one equivalent of glycerol and one equivalent of levulinate, two equivalents of water are formed. Water can conveniently be removed by distillation, or by an azeotropic distillation in the presence of a suitable inert solvent such as hexane, heptane, toluene, benzene, and the like. When about two equivalents of water have been removed from the reaction mixture, the reaction mixture contains predominantly a polymeric levulinate-glycerol ketal adduct comprising a repeat unit having formula (1):

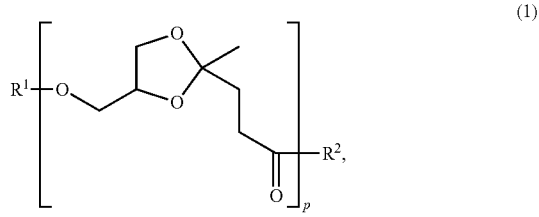

(1)

wherein the $R^1$ is hydrogen or a carboxyl atom of a levulinate fragment, and wherein $R^2$ is hydroxyl, an oxygen atom of a glycerol, or an oxygen atom of an esterified glycerol fragment, and wherein p is an integer.

The product is a polymer that is, in the absence of other compounds and impurities, typically terminated at its ends by a levulinoyl group and by a glycerol ester fragment.

The value of p depends on may factors and may significantly vary, depending on how much water has been removed, the reactant ratio, acid catalyst and severity of the heating conditions used to remove water. The purity of the glycerol and levulinate are also factors. Relatively impure industrial grades of glycerol and levulinate give adducts wherein p is in a range typically between 1 and 10. However, even with pure glycerol and levulinate it is difficult to obtain polymers with p values significantly in excess of 30. It has been found that the direct polycondensation reaction between glycerol and levulinate becomes staggered due to formation of the polymers of formula (1'), wherein $R^1$ is represented by a gamma-valerolactone derivative, as shown herein:

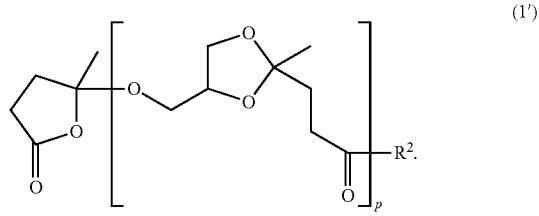

(1')

If heated for sufficiently long time, the compound (1') will slowly rearrange to a levulinoyl-terminated polymer, thereby allowing for further polymer growth. However, in industrial practice, it is not practical or necessary to rely on such long reaction times, and it is preferred that the polycondensation reaction be stopped when about 70 to 95% of the theoretical amount of water has been collected. The resulting polymers comprise glycerol fragments that are esterified at more than one hydroxyl group, and such fragments are recognized herein as points of polymer branching or points of repeat unit inversion, wherein the repeat unit is of formula (1).

Depending on the severity of the conditions of the reaction, some ether bond formation, resulting in diglyceryl fragments, or some elimination of hydroxyl groups from glycerol, to form acrolein, is possible. It is also possible that some angelicalactone formation from levulinate also occurs and this product may be isolated and re-used. Typically, the polymeric adduct of glycerol and levulinate prepared from industrial grade glycerol and levulinate is a very viscous, semi-transparent or transparent liquid with a pale yellowish-brownish to near colorless honey-like appearance due to traces of unidentified byproducts. However, even in the presence of these by-products, the final polymeric adduct comprising the repeat unit of formula (1) is found herein to be useful in the preparation of compounds and various intermediates.

Similarly to the free levulinic acid, levulinic esters of monohydric alkanols, beta- and gamma-angelicalactones, and 4,4-dialkoxypenanoate esters (which are esters of ketals of levulinic acid with monohydric alkanols) are also suitable to practice the synthesis of the glycerol levulinate ketal compounds comprising the repeat unit of formula (1). Any of these levulinic derivatives can be used in the synthesis of the glycerol levulinate ketal compounds in a substantially pure form, or in a mixture. The mixtures can comprise any of the above compounds with a quantity of free levulinic acid. When mixtures of the levulinic derivatives are used to make the glycerol levulinate ketal compounds, it is preferred that about one molar equivalent of these compounds is used per molar equivalent of glycerol.

Similarly, in the synthesis of the glycerol levulinate ketal compounds, some or all of the glycerol can be replaced with a glycerol ketal or acetal of formula (2):

(2)

wherein $R^4$ and $R^5$ are each independently selected from hydrogen; linear, branched, or cyclic alkyl; linear, branched, or cyclic alkenyl; aryl; or aralkyl. Preferably, $R^4$ and $R^5$ are not both hydrogen.

Mono, di and tri esters of glycerol with simple $C_1$-$C_8$ linear or branched alkanoic acids can also be used instead of glycerol, or in a mixture with glycerol. Monolevulinate ester of glycerol is also a suitable starting material.

Synthesis of the condensation polymeric glycerol levulinate ketal adduct comprising the repeat unit of formula (1) of glycerol is carried out with glycerol and levulinic acid, which are fully miscible compounds. For industrial practice, glycerol and levulinic acid do not need to be anhydrous and thus may contain varying amounts of water. However, it is preferred that these starting materials do not contain excessive amounts of water, as this results in a less efficient use of equipment. Typically, glycerol and levulinic acid with water contents of about 10% or less are preferred.

Synthesis of the polymeric levulinate-glycerol ketal adduct comprising the repeat unit of formula (1) typically requires the presence of a suitable acid catalyst. Non-limiting examples of such catalysts include strong mineral acids, such as sulfuric, hydrochloric, hydrofluoroboric, hydrobromic acids, p-toluenesulfonic acid, camphorosulfonic acid, methanesulfonic acid, and like. Various resins that contain protonated sulfonic acid groups are also useful as they can be easily recovered after completion of the reaction. Examples of acids also include Lewis acids. For example, boron trifluoride and various complexes of $BF_3$, exemplified by $BF_3$ diethyl etherate. Silica, acidic-alumina, titania, zirconia, various acidic clays, and mixed aluminum or magnesium oxides can be used. Activated carbon derivatives comprising mineral acid, sulfonic acid, or Lewis acid derivatives can also be used. One of ordinary skill in the art can practice many variations on the part of the catalyst composition and the amounts used in the preparation described herein. Amount and type of catalyst depends on the specific chemical composition of the epoxide and glycerol or glycerol derivative of formula (3), used in the reaction and can be readily established by one skilled in the art. It is preferred, however, that low-cost catalysts that impart minimal or negligible corrosion effects on the equipment used in the synthesis, and have low volatility, toxicity, and environmental impacts, or can be easily neutralized to innocuous compounds, are used. Sulfuric acid is one such preferred catalyst. The reaction of condensation of glycerol and levulinic acid can be carried out without a catalyst, but, for industrial purposes, these reaction conditions are generally too slow to be practical. In order to yield industrial quantities of compounds comprising the repeat unit of formula (1), it is preferred that the condensation be accelerated by use of a catalyst and elevated temperature sufficient to remove water from the reaction mixture without undue time expenditure. The condensation reaction may optionally also be carried out under reduced pressure to facilitate removal of water, and to minimize formation of discolored by-products.

An adduct of glycerol and levulinate comprising ketal fragments of formula (1) can be further subjected to chemical reactions to yield derivatives of glycerol and levulinate.

Trans-esterification with Alcohols

Products can be obtained when polymeric compounds comprising the repeat units of formula (1) are treated under trans-esterification conditions with a monohydric alcohol. Typically, such reactions are carried out with an alcohol in the presence of a base, such as alkali or alkali-earth hydroxides or alkoxides. The catalyst can be used in a soluble or insoluble form. Many trans-esterification base catalysts are known in the art, and the present disclosure is not limited to the use of a particular catalyst.

Such trans-esterification reactions can result in the formation of a mixture of cis- and trans-stereoisomers of a hydroxyester compound having formula (3):

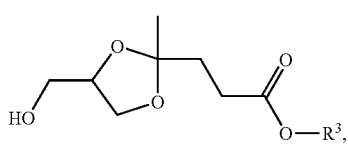

(3)

wherein $R^3$ is a linear, branched, or cyclic alkyl or alkenyl, aryl, aralkyl, or alkyloxyalkyl.

A typical procedure for making the hydroxyester of formula (3) involves use of an excess of alcohol which, after neutralization of the base catalyst, is removed by distillation. The trans-esterification reaction with an alcohol typically also results in the formation of minor quantities of free glycerol that readily separates as an alcohol-immiscible liquid from the alcoholic solutions of hydroxyester (3), ester of levulinic acid, and the $R^3OH$ alcohol used in the trans-esterification. The latter compound can be readily separated from the hydroxyester of formula (3) by distillation, typically under reduced pressure, and, if desired, re-used in the synthesis of the glycerol-levulinate ketal polymeric adduct comprising the repeat unit of formula (1).

It has been found that the cis- and trans-isomers of the compound of formula (3) can be readily separated from each other by distillation using ordinary distillation equipment known in the art, such as distillation columns with sufficient number of plates, falling film distillation columns, and the like. Preferably, distillation to separate cis- and trans-isomers of the compound of formula (3) is carried out under reduced pressure and in the relative absence of a trans-esterification catalyst. The latter condition is beneficial as it minimizes polymerization of the compound of formula (3), as well as formation of a free alcohol, $R^3OH$, which can make maintenance of sufficient vacuum difficult. However, the distillation may be carried out without complete removal of trans-esterification catalyst, and any undistilled oligomers can be recovered and re-used for preparation of the compound of formula (3) by the base-catalyzed reaction disclosed above.

It has also been found that alkaline trans-esterification reaction of ketal-ester co-polymers of glycerol and levulinate comprising the repeat units of formula (1) yield mixtures of reaction products that largely comprise the cis and trans-isomers of the compounds of formula (1), which are 1,2-ketals of glycerol and a levulinate ester with alcohol $R^3OH$. Only negligible traces of 1,3-glycerol ketals of esterified levulinate are found in such product mixtures.

Trans-esterification with Carboxylic Esters

In a related embodiment, the trans-esterification in the presence of base is carried out under conditions similar to that described above for an alcoholic trans-esterification, except that instead of an alcohol, an ester of a carboxylic acid and an alkanol is used. In this case, stereoisomers of carboxylic esters of glycerol levulinate ketal of formula (4) are formed:

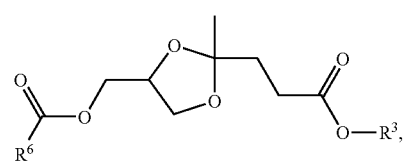

(4)

wherein $R^3$ is a linear, branched, or cyclic alkyl or alkenyl, aryl, aralkyl, or alkyloxyalkyl, and $R^6$ is hydrogen, or is a linear, branched, or cyclic alkyl or alkenyl, aryl, aralkyl, alkyloxyalkyl, or oxoalkyl.

The synthesis of compound (4) using trans-esterification with the carboxylic ester is also typically accompanied by the formation of minor quantities of levulinate ester, glycerol, glycerol mono, di and tri esters of the carboxylic acid. $R^6COOH$, and of varying quantities of the compound of formula (3). The quantity of the compound of formula (3) depends largely on the value of p specified in the structure of the repeat unit of formula (1) described above; polymeric ketal adducts having lower values of p tend to produce higher relative quantities of the compound of formula (3) in relation to the compound of formula (4). The reaction products from base-catalyzed trans-esterification with carboxylic esters are typically separated and purified by distillation.

De-polymerizing Trans-esterification of Polymeric Glycerol Levulinate Ketal Adducts In another embodiment, a polymer comprising a glycerol levulinate ketal adduct comprising a unit of formula (1a):

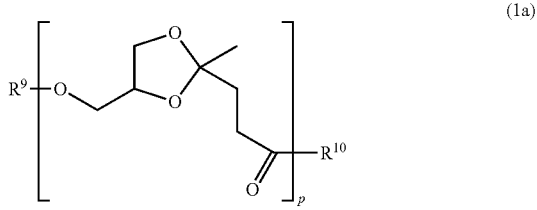

wherein $R^9$ is hydrogen or a carboxyl moiety; $R^{10}$ is $OR^{11}$, or $N(R^{12})_2$; $R^{11}$ and $R^{12}$ are independently hydrogen or a linear, branched, or cyclic alkyl; and p is an integer. In some embodiments, $OR^{11}$ can be a fragment of a monohydric or a polyhydric alcohol. The compound comprising the unit of formula (1a) is subjected to a trans-esterification reaction, resulting in a depolymerization that provides for the formation of a bicyclic lactone-ketal adduct of glycerol and levulinate, named herein "segetolide" ("lactone of a crop field"), having formula (5):

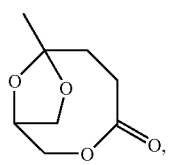

7-methyl-3,8,10-trioxabicyclo[5.2.1]decan-4-one.

A further embodiment includes the provision of a cyclic dimer of segetolide (5). Such a cyclic dimer (named herein "bis-segetolide") is a cyclic bis-lactone (diolide) bis-ketal having formula 5(a):

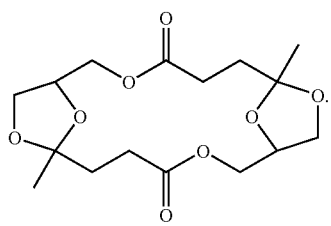

Typically, such a depolymerizing trans-esterification reaction is carried out under substantially anhydrous reaction conditions, and in the presence of an acid or a base catalyst. Alternatively, one or more of many other catalysts known in the art to catalyze esterification or trans-esterification reactions, such as those known in the art of synthesis of various polyesters, may be used. Numerous examples of catalysts for synthesizing of compounds of formulae (5) and/or (5a) by depolymerization of polymers comprising repeat units of formula (1a) can be found in the art of polyester synthesis. Description of such catalysts and methods of their use can be found, for example, in U.S. Pat. Nos. 4,133,800, 4,205,157, 4,208,527, 5,028,667, 5,095,098, 5,210,108, 5,208,297, 5,202,413, 5,292,859 5,342,969, 5,565,545, and 6,828,272.

Under such conditions, the cyclic ketal lactones of formulae (5) and/or 5(a) are in equilibrium with one another, the polymeric compound, and various oligomers comprising the unit of formula (1a). Under sufficient temperature, typically in the range of 160-300° C., and, preferably, under reduced pressure, a vapor phase comprising ketal lactones of formulae (5) and (5a) is formed. The compounds of formulae (5) and (5a) are typically separated from the reaction mixture by distillation under reduce pressure, and separated from each other, if desired, by distillation. Further purification of the compounds of formulae (5) and (5a) can be achieved by repeated distillations, or by using a high efficiency distillation column. By adjusting the temperature and pressure of the distillation, it is possible to obtain the compound of formula (5) substantially free of the compound of formula (5a) without difficulty, as these two compounds have a large difference in boiling temperatures. It is understood that if an effective trans-esterification catalyst is present in the preparation of substantially pure compounds of formula (5) and/or 5(a), such compounds may equilibrate to form a mixture of these to compounds, as well as varying quantities of polymers comprising the cis-isomers of the units of formula (1b):

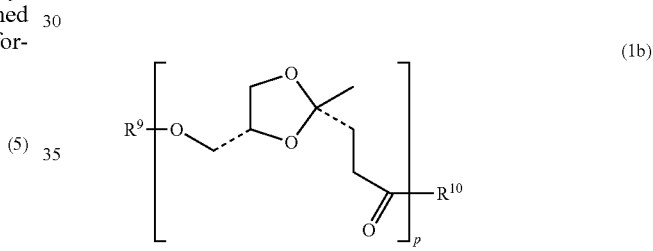

wherein $R^9$ is hydrogen or a carboxyl moiety; $R^{10}$ is $OR^{11}$, or $N(R^{12})_2$; $R^{11}$ and $R^{12}$ are independently hydrogen or a linear, branched, or cyclic alkyl; and p is an integer. In some embodiments, $OR^{11}$ can be a fragment of a monohydric or a polyhydric alcohol.

When depolymerization is conducted in the presence of a catalyst, using a polymer comprising a mixture with approximately equal quantity of cis- and trans-units of formula (1), approximately half of the quantity of the polymeric adduct comprising the cis- and trans-isomeric units of formula (1) can be converted to the compound of formula (5). The remainder of the undistilled polymeric adduct consists predominantly, or exclusively, of the units of formula (1) having the trans-stereochemistry (1c):

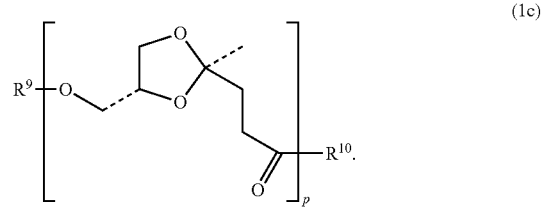

wherein $R^9$ is hydrogen or a carboxyl moiety; $R^{10}$ is $OR^{11}$, or $N(R^{12})_2$; $R^{11}$ and $R^{12}$ are independently hydrogen or a linear, branched, or cyclic alkyl; and p is an integer. In some embodiments, $OR^{11}$ can be a fragment of a monohydric or a polyhydric alcohol.

During depolymerization of polymers comprising the unit of formula (1a) conducted in the absence of an effective amount of an acid catalyst that allows the trans-ketal to re-equilibrate to a mixture of cis- and trans-ketals, the compounds of formulae (5) and (5a) are formed only from the cis-isomers of units of formula (1b).

In general, the quantity of the products of compound of formulae (5) and (5a) that can be produced is limited by the abundance of the cis-fragments of the formula (1b) in the polymer used for depolymerization.

When depolymerization of the polymer comprising units of formula (1) is conducted in the presence of an acid catalyst, both cis- and trans-isomers of the units are in quilibrium, and thus both cis- and trans-units can be converted to the compound of formula (5) and/or 5(a). It is preferred, however, that when an acid catalyst is used to conduct the depolymerization reaction, the temperatures of the reaction not be allowed to exceed 120-130° C. to avoid excessive decomposition of glycerol to acrolein, and formation of glyceryl ethers.

After the compounds of formula (5) and/or (5a) have been substantially removed by distillation, the resulting depolymerization product is a useful polymer typically comprising predominantly, or exclusively, the trans-fragments of formula (1c). Such can be further converted, for example, by using trans-esterification with an excess alcohol or an ester in the presence of base. Under such conditions, compounds of formula (3) and (4) comprising predominantly, or exclusively, the trans-isomers of the compounds of formula (3a) and (4a), respectively, are thus prepared:

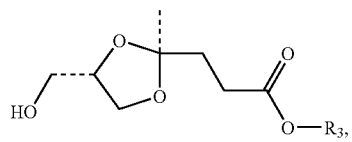

(3a)

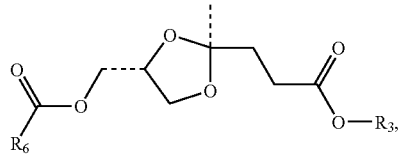

(4a)

Similarly, the bicyclic lactone ketal compounds of formula (5) and/or 5(a) are readily converted by a base-catalyzed trans-esterification with an alcohol or an ester to the corresponding cis-isomers of the hydroxyester (3b) and diester (4b):

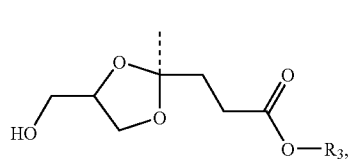

(3b)

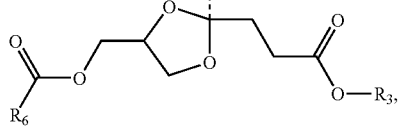

(4a)

The glycerol ketal derivatives of levulinic esters of formula (3), (4), (5), and 5(a), as well as the separated individual cis- and trans-stereoisomers (3a), (3b), (4a), and (4b), are excellent solvents for a variety of both hydrophobic compounds (e.g., fats, oils, greases, waxes, varnishes) and many hydrophilic compounds. Compounds of formula (3), wherein $R^3$ is a $C_1$-$C_5$ lower alkyl, are miscible with water in a broad range of concentrations. Therefore, these compounds are useful as part of various formulations in applications such as degreasing, paint thinners, paint removal or as part of formulated adhesives. Because of their relatively slow evaporation under ordinary environmental conditions (which can be controlled by selecting appropriate length of $R^6$ and $R^3$ groups), and because of a low agreeable or negligible odor, these compounds are also useful as coalescent solvents in various latex paints and coatings where they can be supplied to the formulation in addition to, or instead of, typical petroleum-derived solvents such as 2,2,4-trimethyl-1,3-pentanediol monoisobutyrate or diisobutyrate, ketones, and aromatic hydrocarbons.

The compounds (3) and (4), as well as any individual or mixed stereoisomers thereof, have also been found to be useful as plasticizers with various polymers, such as poly(vinyl chloride), poly(3-hydroxyalkanoates), poly(3-hydroxybutyrate), poly(lactate), and polysaccharides.

Poly(vinyl chloride) polymers, PVC, are homopolymers or co-polymers of vinyl chloride. Many PVC compounds of various degree of polymerization, cross-linking and co-polymer composition are known in the art and are produced industrially.

Poly(3-hydroxyalkanoates), PHA, are polyester homopolymers or co-polymers of 3-hydroxyalkanoic acids. Preferably, PHA is composed of linear 3-hydroxyalkanoic fragments having from 3 to 18 carbon atom atoms. Poly(3-hydroxybutyrate), PHB, is a homopolymer that is produced biologically, for example by various microorganisms. A pure PHB polymer is a brittle polymer having a narrow range of processing temperatures, and it decomposes readily at temperatures that are only 20-30° C. above its melting temperature.

Poly(lactate), or poly(lactide), PLA, is a known polyester homopolymer comprising repeat units of lactic acid of various stereochemistry.

Polysaccharides are homopolymers and co-polymers, linear or branched, comprising hexose or pentose fragments connected via glycosyl linkages. The polysaccharides may optionally contain various additional groups such as acylamido groups, sulfate ester groups, carboxylic ester groups, alkyl and hydroxyalkyl ether groups and the like. Such additional groups may be present in polysaccharides derived from natural sources or can be artificially introduced (i.e., by acylation of cellulose). Examples of polysaccharides include acylated derivatives of cellulose and starch, as well as native or acylated chitin and pectin.

Plasticizers are chemical compounds added to a base composition comprising one or more of the above polymers with the purpose of lowering the glass transition temperature of the polymer composition, thereby making the composition more flexible and amenable to processing, e.g., by melt extrusion or molding. Plasticizers are typically used at various effective concentrations, and depending on the polymer used and desired properties of the compounded polymer formulations, plasticizers can be used at concentrations between 1 and 80% by weight of the unplasticized polymer. It is understood that, depending on the polymer and the plasticizer used, plasticizers can also confer other changes in physical and mechanical properties of the compounded polymer, as well as changes in barrier properties of the compounded polymer in respect to its permeability for various gases, water, water vapor, or organic compounds. It is also understood that one or more different plasticizers can be used in various blends with additional compounds for the preparation of an extrudable or moldable polymer composition. Such additional compounds can include various inorganic and organic filler compounds, wood dust, reinforcing fibers, dyes, pigments, stabilizers, lubricants, anti-microbial additives, and the like.

Plasticizers are typically mixed with a polymer by mixing at temperatures that are above or below the melting point of the polymer. Plasticizers can also be introduced with a help of an optional volatile solvent. Many variations of techniques for introducing plasticizer compounds to polymer compositions are known in the art, For use as plasticizers, compounds of formula (3) and (4) are preferably selected from compounds wherein $R^3$ and $R^6$ are $C_1$-$C_{23}$ linear or branched alkyls, and preferably $C_1$-$C_{12}$. Specific choices for $R^3$ and $R^6$ depend on the polymer selected for plasticization and on the intended properties and application.

The glycerol ketal levulinic adducts of formula (3), (4), and (5a) are useful as plasticizer compounds for PVC, poly(3-hydroxyalkanoates), poly(lactate), and various polysaccharide polymers. Compounds of formula (3), (4) and (5a) are compatible with these polymers across a broad range of concentrations. Compounds of formula (4) and (5a) are preferred for plasticization of PVC, as plasticizers with a substantial content of free hydroxyl group are generally not desired in compounded PVC resins due to stability problems of the PVC resin. By selecting various $R^3$ and $R^6$ moieties in the reactants used in the synthesis of these adducts, it is also possible to fine-tune the properties of the plasticizer not only in respect to best plasticization properties and best compatibility, but also in respect to the barrier properties of the resulting polymer, e.g., its permeability to moisture, gases, solvents, water leaching, and odor and stain retention. Depending on the desired properties, compounds of formula (3), (4), and (5a) can be used at various concentrations, typically, between 5 and 80% by weight of the plasticized polymer composition. However, in practice it is sufficient to provide 5 to 25% by weight plasticizer to achieve significant lowering of the glass transition point and thus obtain useful polymeric compositions. The plasticizer compounds (3), (4), and (5a) can be used as individual compounds or as mixtures, including mixtures comprising other plasticizers known in the art such as aromatic and aliphatic dicarboxylic esters, epoxidized triglycerides, and the like.

Synthesis of Polymeric Glycerol Levulinate Ketal Compounds from the Monomers of Formulae 3-5

The compound of formula (5) and the compounds of formulae (3) and (4), inclusive of compounds with defined cis- or trans-stereochemistry, such as (3a), (3b), (4a), (4b), can be further polymerized to provide for a variety of co-polymer compositions of glycerol and levulinate having at least one unit of formula (6):

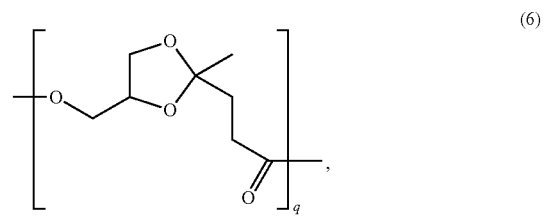

wherein q is an integer.

The cyclic ketal-lactone compounds of formula (5) and (5a) are particularly suitable for use in polymerization under ring opening living polymerization conditions. Such conditions are well known in the art and are known to yield high molecular weight melt-processable polymers suitable for a variety of uses in the manufacturing of various plastics and fibers. For example, U.S. Pat. Nos. 5,028,667, 5,292,859, 5,095,098, and 5,210,108 contain descriptions of catalysts and methods of use suitable for carrying out living polymerization of various lactones and mixtures thereof. Similarly, *J. Macromolecules* (2001, 34, 8641-8648) contains a description of conditions and catalysts for polymerizing dioxanones. These conditions and catalysts have been found to be useful in the polymerization or co-polymerization of compounds of formula 5 and/or 5(a) to form perfectly alternating ketal-ester copolymers of glycerol and levulinate comprising the cis-unit of formula (1b). Such polymers are clear thermoplastic transparent polymers that can be obtained in a practically colorless form and can be melt-processed, extruded, cast, and rolled to a variety of shapes.

Synthesis of polymers comprising the unit of formula (6) are not limited to living polymerization. The hydroxyesters (3) and diesters (4) can also be converted to useful polymers comprising at least one unit of formula (6) by a polycondensation reaction in the presence of a suitable catalyst. The art of synthesis of various polyesters by polycondensation is old and many examples of suitable catalysts are known. It has been found that many known catalysts for the synthesis of polyesters can be used to make polymers comprising at least one unit of formula (6). Non-limiting examples of suitable catalysts include alkali and transitional metal alkoxides, germanium oxide, alkali metal alkoxides, sodium, and acids. Further examples include various alkoxides of titanium and tin (II) octanoate. Other descriptions of catalysts and methods of their use can be found, for example, in U.S. Pat. Nos. 4,133,800, 4,205,157, 4,208,527, 5,028,667, 5,095,098, 5,210,108, 5,208,297, 5,202,413, 5,292,859 5,342,969, 5,565,545, 6,828,272, and references cited therein.

The compounds of formulae (3) and (4), inclusive of compounds with defined cis- or trans-stereochemistry, such as (3a), (3b), (4a), and (4b), are typically polymerized in the presence of an effective quantity of a polycondensation catalyst, and under conditions allowing for the removal of an alcohol ($R^3OH$) or an ester ($R^6COOR^3$) by distillation. For polymerization of these compounds, it is preferred (but not necessary) that the $R^3OH$ alcohol is a primary or secondary alcohol, and it is also preferred that the ester of formula $R^6COOR^3$ and/or the alcohol $R^3OH$ that form during polycondensation have boiling points sufficiently below the boiling point of the monomers of formula (3), (4), and/or (5) so that they can be removed with ease from the body of the forming polymer.

The polymerization reactions can be carried out in the presence of an inert solvent, or in a neat form. Preferred non-limiting examples of solvents are hydrocarbons, halogenated hydrocarbons, and ethers.

The properties of the resulting polymers differ, depending on the degree of polymerization and the stereochemistry of the monomers used in their synthesis.

The ester-ketal polymers of glycerol and levulinate comprising the unit of formula (6) are useful as polymeric plasticizers with various polymers. For example, these polymers are used for plasticizing PVC, polyesters such as PHA, PHB, and PLA, and polysaccharides such as acylated cellulose. For plasticization of these polymers, the ester-ketal polymers of glycerol are blended with unplasticized polymers typically at elevated temperatures sufficient to melt or soften the ingredient with the highest melting point, and preferably, under inert atmosphere (to minimize any decomposition of the polymer plasticized). Plasticization with these compounds can also be accomplished with the aid of a solvent that is typically removed after a homogeneous blend is obtained. Plasticized compositions may contain other additives such as stabilizers, inorganic and organic fillers, reinforcing fibers, pigments, dyes, and the like. Plasticized compositions comprising the polymers having ester-ketal repeat units of formula (6) can be cast or molded or extruded into films, fibers, tubing, pipes, and other objects of various shapes that are typically used to produce various consumer and industrial products from other known plasticized compositions of PVC, PHA, PHB, PLA, and polysaccharides.

Reaction of Glycerol Levulinate Ketal Compounds with Epoxides of Normal Alpha-olefins In another embodiment, the compounds of formula (3) are reacted with epoxides. Preferably, the compounds of formula (3) are esters and not free acids or salts. The epoxides are epoxides of normal alpha-olefins (NAO) or epoxidized unsaturated fatty acid esters.

The first set of reaction products can be formed by the reaction of compounds of formula (3) and NAO epoxides. The resulting products have a formula (7):

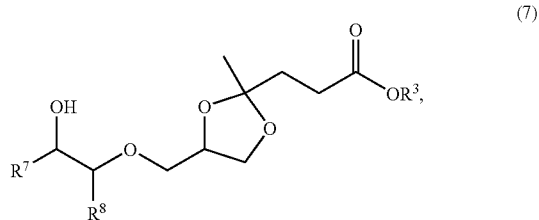

(7)

wherein $R^3$ is a linear, branched, or cyclic alkyl or alkenyl, aryl, aralkyl, or alkyloxyalkyl, and one of $R^7$ or $R^8$ is hydrogen and the other is a $C_6$-$C_{30}$ linear alkyl. Preferably, a $C_6$-$C_{14}$ linear alkyl.

Compounds of formula (7) are prepared from the 1,2-epoxides of NAO having formula (8):

(8)

wherein $R^9$ is a $C_6$-$C_{30}$ linear alkyl, and preferably, a $C_6$-$C_{14}$ linear alkyl.

The compounds of formula (8) are reacted with the compounds of formula (3) in the presence of an acid catalyst, and optionally, an inert co-solvent.

Typically, catalysts for reacting epoxides with the compound of formula (3) include various acids that are known in the art. Such conditions are generally applicable to the reactions of the compound of formula (3) with epoxidized unsaturated fatty acid esters. Non-limiting examples of such catalysts include strong mineral acids, such as sulfuric, hydrochloric, hydrofluoroboric, hydrobromic acids, p-toluenesulfonic acid, camphorosulfonic acid, methanesulfonic acid, and like. Various resins that contain protonated sulfonic acid groups are also useful as they can be easily recovered after completion of the reaction. Examples of acids also include Lewis acids. For example, boron trifluoride and various complexes of $BF_3$, exemplified by $BF_3$ diethyl etherate, are also useful. Examples of other Lewis acids include anhydrous $SnCl_2$, $SnCl_4$, $TiCl_4$, $AlCl_3$, silica, acidic alumina, titania, zirconia, various acidic clays, mixed aluminum or magnesium oxides, and the like. Activated carbon derivatives comprising mineral acid, sulfonic acid, or Lewis acid derivatives can also be used.

The present disclosure is not limited to a specific catalyst or an amount of catalyst. One of ordinary skill in the art can practice many variations on the part of the catalyst composition and the amounts used in the preparation described herein. Elevated temperatures may be used to accelerate the reaction with less reactive catalysts, however, the temperature of the reaction mixture is not critical for succeeding in making a quantity of the glyceryl ether product, as even with less active catalysts the reaction still proceeds to yield the desired compounds. Amount and type of catalyst depends on the specific chemical composition of the epoxide and of the compound of formula (3) used in the reaction, and can be readily established by one skilled in the art.

The reaction with epoxides can be carried out in the presence of an optional co-solvent that is inert under reaction conditions and is typically removed at the end of the reaction by distillation. Typically, it is desired to use a sufficient quantity of a co-solvent or a reactant, such as the compound of formula (3), to minimize cross-linking of the epoxides via ether bond formation. Non-limiting examples of suitable co-solvents include saturated hydrocarbons, ethers, and polyethers. Typically, any excess solvent and un-reacted starting material are removed after completion of the reaction by distillation at normal or reduced pressure. It is also preferred to neutralize or otherwise remove the acid catalyst prior to distillation.

Because the compounds of formula (3) are very good solvents for NAO epoxides, the reaction between epoxide and the glycerol derivative of formula (3) can also be conveniently conducted in the excess of the latter compound, typically at 2 to 20 times molar excess. When insufficient excess of the compound (3) is used, oligomeric polyether adducts of epoxide and the compound of formula (3) are formed.

The compounds of formula (7) are further converted by saponification to the alkali or alkali-earth metal salts of the carboxylic acid having formula (7a).

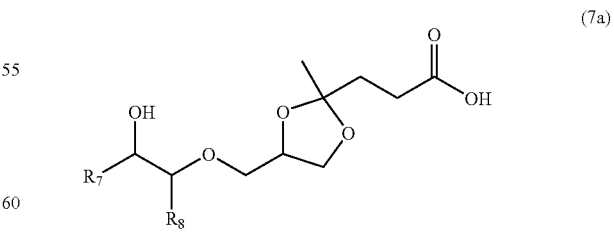

(7a)

Saponification is typically carried out in water or water-alcohol mixtures in the presence of a sufficient amount of alkali or alkali-earth metal hydroxide or carbonate, and after removal of any excess of the compound of formula (3) and/or co-solvent, e.g. by distillation under reduced pressure. The salts of the compound of formula (7a) can be stored and used in an aqueous solution, or, after evaporation of water and any volatile co-solvents, in a substantially anhydrous neat form.

Reaction of Glycerol Levulinate Ketal Compounds with Epoxides of Unsaturated Fatty Acid Esters Another set of compounds is provided herein by using reaction of the compound of formula (3) with epoxides of unsaturated fatty acid esters. Preferably, the compounds of formula (3) are esters and not free acids or salts. These epoxides are prepared in the manner substantially similar to the above-described methods for making compounds of formula (7) from the NAO epoxides of formula (8).

Unsaturated fatty acids mean linear monocarboxylic acids having from 10 to 24 carbon atoms and at least one double bond. The double bonds can be in any position, conjugated with each other or non-conjugated, but not in allenic arrangements, and any of the double bonds can be independently cis or trans. Preferably, unsaturated fatty acids have one to three double bonds. Fatty acids can also be composed of a mixture of various unsaturated and saturated fatty acids, for example, as in the triglycerides of various vegetable oils, fish oils, and palm oils.

Esters of unsaturated fatty acids mean esters of the above-described fatty acids with monohydric or with polyhydric alcohols.

Monohydric alcohols are linear or branched primary or secondary alkanols or alkoxyalkanols having from 1 to 12 carbon atoms. Preferred examples of alkanols are methanol, ethanol, propanol, isopropanol, butanol, secondary butanol, isobutanol, isoamyl alcohol, 2-ethylhexanol. Preferred alkoxyalkanols are primary or secondary alcohols having from 3 to 12 carbon atoms, wherein a linear, branched, or cyclic alkoxy group having from 1 to 8 carbon atoms is located at a vicinal position to the hydroxyl group. Such alkoxyalkanols are typically derived by opening an alkyl oxirane with an alkanol. Another suitable example of an alkoxyalkanol is tetrahydrofurfuryl alcohol readily accessible via hydrogenation of furfural. The most preferred are monohydric alcohols due to their availability, cost and satisfactory stability of their esters.

Polyhydric alcohols are linear or branched polyhydroxylated alkanes having from 1 to 6 hydroxyl groups. Typical examples are ethylene glycol, propylene 1,2- and 1,3-diols, butylene glycol isomers, glycerol, 1,2,4-trihydroxybutane, pentaerythritol, xylitol, ribitol, sorbitol, mannitol, and galactitol. Polyhydric alcohols can optionally contain one or more ether bonds, and suitable examples of such polyhydric alcohols are isosorbide, sorbitane isomers, and diglycerol.

It is preferred that substantially all hydroxyl groups of the polyhydric alcohol are esterified with an unsaturated fatty acid group. It is understood that in the industrial practice it may not be practical to achieve a full esterification. It is also understood that in the industrial practice, where mixed fatty acid compositions are used, not all of the fatty acid groups can be unsaturated and some fully saturated fatty acid groups can be present. In fact, it is cost-advantageous to use mixtures of unsaturated and saturated fatty acid esters such as present in triglycerides of typical vegetable oils (e.g. soybean oil, linseed oil, canola oil, safflower oil, sunflower oil, corn oil, castor oil, their blends and the like). It is preferred, however, that the mixed fatty acid esters contain predominantly unsaturated fatty acid esters. It is also preferred that a fatty acid ester with a high content of mono-unsaturated fatty acid ester is used, such as compositions found in high oleic canola oil. Esters of 10-undecylenic acid are also preferred. Another preferred starting material is a mixture of methyl esters of fatty acids derived by trans-esterification of vegetable oils (e.g., of soybean oil, canola oil and other unsaturated triglycerides commonly used in the industrial production of various biodiesel fuels).

Various unsaturated fatty acid esters can be optionally blended, mixed, partially hydrogenated, or otherwise isomerized to change position or stereochemistry of the double bonds.

Epoxidized unsaturated fatty acid ester means that at least one of the double bonds of the unsaturated fatty acid ester is oxidized to an epoxy group. Such oxidations are well known in the art and can be readily accomplished in an industrial scale, e.g., by using hydrogen peroxide and a carboxylic acid (e.g., formate or acetate), or by the halohydrin method. It is preferred, however, that epoxidation of a majority or all of the double bonds present in the unsaturated fatty acid ester is accomplished. It is understood that in practice, epoxidized fatty acid esters may contain various quantities of by-products arising from hydrolysis or rearrangement of epoxides and from cross-linking of the fatty acid chains. Use of epoxidized fatty acid esters containing small quantities of epoxidation by-products and epoxide decomposition by-products is fully within the scope of the present disclosure.

Ethers derived from epoxides of mono-unsaturated fatty acid esters and compound of formula (3) have formula (9):

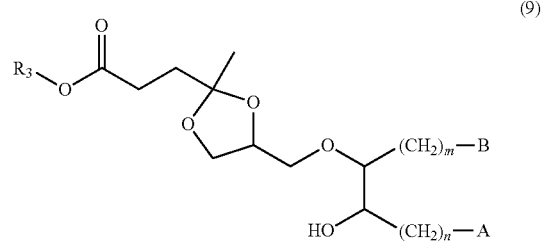

(9)

wherein $R^3$ is a linear, branched, or cyclic alkyl or alkenyl, aryl, aralkyl, or alkyloxyalkyl, one of A or B is H and the other is an esterified carboxyl, and n and m are integers each having values from 0 to 20, and the value of the sum of m+n is in the range from 8 to 21.

When bis-epoxides or tris-epoxides of unsaturated fatty acid esters having epoxy groups positioned in a close proximity to each other are used, an intra-molecular epoxide opening reaction takes place, resulting in the formation of one or more ether bonds each connecting two carbon atoms of the continuous fatty acid carbon chain. Typically, such ether bonds result in the formation of a tetrahydrofuran (major) and tetrahydropyran (minor) rings. Thereby forming complex mixtures of the stereoisomers of oxygenated derivatives of unsaturated fatty acid esters comprising pendant ether groups derived from the compound of formula (3).

For example, representative isomers of the such surfactant products from a bis epoxide derived from a di-unsaturated fatty acid having two double bonds separated by a methylene group have formulae (10a) and (10b):

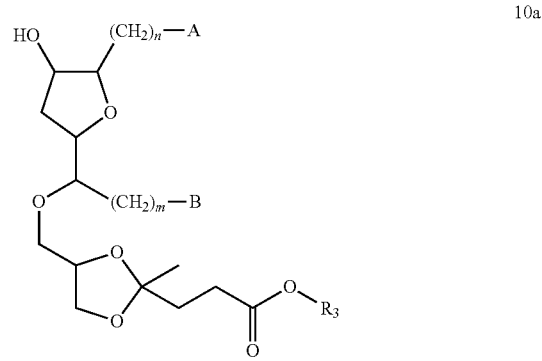

10a

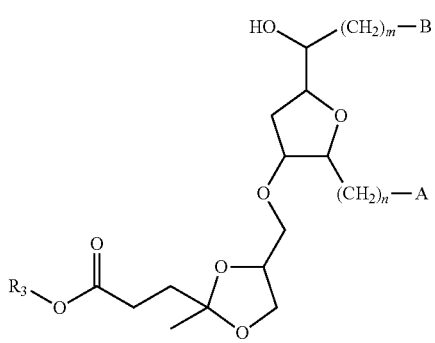

(10b)

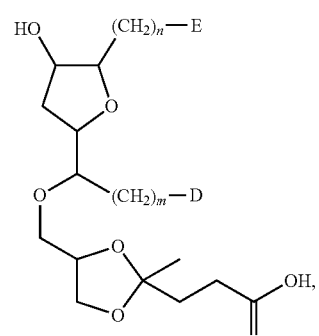

(12a)

Compounds of formula (10a) and (10b) are typically formed as mixtures that also comprise other adducts such as di(glyceryl levulinate ketal) ether adducts resulting from opening of each of the epoxy groups with a different molecule of the compound of formula (3), resulting in oxygenated fatty acid derivatives comprising two hydroxyl groups and two pendant ether (glyceryl levulinate ketal) groups.

Preferably, the ether adducts of epoxidized fatty acid esters are formed by the reaction of the compound of formula (3), in the presence of a catalyst, followed by the removal of any excess compound of formula (3) and any co-solvent by distillation under reduced pressure.

Alternatively, the adducts of epoxidized unsaturated fatty acid esters and compound of formula (3) can be prepared by treating epoxidized triglycerides with the compound of formula (3) in the presence of a catalyst. In such alternative embodiment, triglyceride polyol compounds are formed. These compounds have free secondary hydroxyl groups and (glyceryl levulinate ketal ester) ether pendant groups attached to the fatty acid chains. Optionally, ether bonds may also be present in such adducts and the ether bonds can connect two carbon atoms of one fatty acid chain (thereby forming a tetrahydrofuran or tetrahydropyran ring) or two different fatty acid chains.

Such adducts of glycerol, or of a ketal/acetal protected glycerol, with the epoxidized triglycerides are typically prepared from known in the art epoxidized soybean oil, linseed oil, and the like. These adducts are found herein to be useful to produce compounds of formulae (9), (10a), and (10b). The conversion of the triglyceride adducts to the compounds of formulae (9), (10a), and (10b) can be accomplished by a trans-esterification reaction with a monohydric alkanol in the presence of a catalytic amount of base. The non-limiting examples of suitable bases are hydroxides of alkali or alkali-earth metals or alkoxides of alkali metals and alkanols.

The carboxyl group in the ether adducts of compound (3) and the hydroxylated fatty acid esters can be further subjected to saponification to furnish a salt (typically, alkali, alkali-earth, ammonium, or amine salt of the dicarboxylic compounds having formulae (11), 12(a), and 12(b):

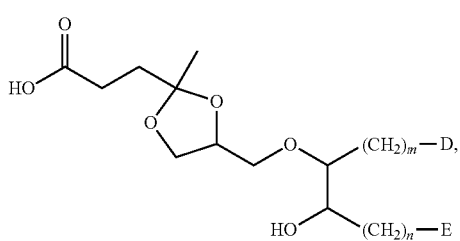

(11)

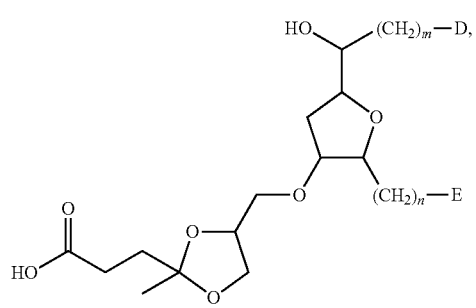

(12b)

wherein one of E or D is hydrogen and the other is carboxyl. Alternatively, the salt compounds of formulae (11), 12(a), and 12(b) are obtained by direct saponification of the adduct of the compound of formula (3) with epoxidized triglycerides.

The carboxyl group of the compounds of formula (7a), (11), 12(a), and 12(b) or of the compounds of formulae (7), (9), (10a), and (10b) can also be amidated with a primary or a secondary alkylamine or an aminoalcohol.

The alkali metal salts, alkali-earth metal salts, amine or ammonium salts, and amides of the carboxylic acids of formulae (7a), (11), 12(a), and 12(b) are useful ionic mild surfactants that can be used in various formulations.

The surfactants derived from the carboxylic acids of formulae (7a), (11), 12(a), 12(b) are stable in cold and hot aqueous solutions in a broad range of pH (e.g., pH 4 to pH 13). Their surfactant, emulsifying, and micelle-forming properties are not negatively affected by the presence of alkali-earth metal ions in the solution. This makes them useful in formulations intended for use in hard water.

These compounds of can be used alone or in various combinations with other surfactants, solvents, glycols, polyols, fragrances, colors, biologically-active and inert additives, enzymes, and wetting agents that constitute the base compositions of preparations used in cleaning, dishwashing, laundry, cosmetic and personal care products, degreasing preparations, and the like. Effective concentrations for use of the surfactant compounds of compounds derived from the carboxylic acids of the formulae (7a), (11), 12(a), and 12(b) depend on the intended use of the formulation and can be easily established empirically by one of ordinary skills in the art. The effective concentrations for these compounds typically range from 0.001% to 100% of the formulated product.

It has also been found that compounds of formulae (7), (9a), (10a), (10b), and the adduct of the compound of formula (3) with epoxidized triglycerides are also useful as plasticizers for PVC, polyesters such as PHA, PHB, PLA, and polysaccharides.

Co-polymers of Glycerol Levulinate Ketals with Other Monomers

In another embodiment, glycerol ketal monomers selected from compounds having formulae (3), (4), (5) and (5a), and any stereoisomers thereof, can be used in the synthesis of co-polymers with a variety of other monomers known in the art. It has been found that copolymers comprising the ketal repeat units of formula (1a) have a broad range of physical properties, and can be prepared through a condensation or trans-esterification reaction of the monomers of formulae (3), (4), (5), and (5a) with one or more compounds selected from various polyhydric alcohols, di and tri-carboxylic acids, hydroxyacids, and cyclic esters.

Non-limiting examples of useful polyhydric alcohols include dihydric alcohols of linear or branched alkanes having from 2 to 20 carbon atoms, glycerol, diglycerol, isosorbide, sorbitol, xylitol, erythritol, pentaerythritol, trimethylolethane, trimethylol propane, diethylene glycol, neopentyl glycol, polyethers such as hydroxyl-terminated poly(ethyleneoxide), poly(propyleneoxide), and the like.

Examples of suitable dicarboxylic acids include either free acids, lower alkyl esters, or anhydrides of succinic acid, maleic acid, adipic acid, isomers of phthalic acids, trimellitic acid, citric acid, itaconic acid, and isomers of naphthalene dicarboxylic acid.

Examples of hydroxyacids and esters thereof can also be used as co-polymers, and can include lactic acid, glycolic acid, 3-hydroxypropionic acid, and 3-hydroxyalkanoic acids.

Hydroxyacids can be further exemplified by hydroxylated derivatives of fatty acids and esters thereof, including triglycerides. Such hydroxylated fatty acid esters including polyhydric hydroxyl derivatives known in the art have been obtained, for example, by reacting epoxidized fatty acid esters with one or more compounds having a hydroxyl group, wherein one or more of the oxirane groups is subjected to an epoxide opening reaction.

Suitable hydroxyacids can be further exemplified by hydroxylated aromatic carboxylic acids such as hydroxylated benzoic acids, toluic acids, naphthoic acids, cinnamic acids, ferrulic acid, and the like.

Lactide, glycolide, 1,4-dioxan-2-ones, alkylated 1,4-dioxan-2-ones, epsilon-caprolactone, and 1,4-dioxepan-2-ones are suitable non-limiting examples of cyclic esters.

Among other suitable co-monomers for making co-polymers of glycerol levulinate ketals comprising the repeating units of formula (1a) include compounds of formulae (7), (9), (10a), (10b), and also, compounds of formula (7b):

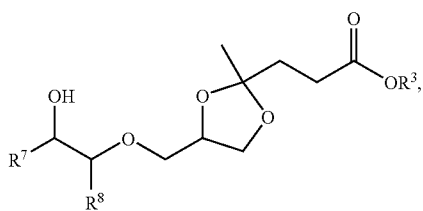

(7b)

wherein $R^3$ is a linear, branched, or cyclic alkyl or alkenyl, aryl, aralkyl, or alkyloxyalkyl, and one of $R^7$ or $R^8$ is H and the other is hydrogen or a $C_1$-$C_{30}$ linear alkyl.

Compounds of formula 7b), compounds with linear alkyls of shorter than 6 carbon atoms can be prepared by reacting compounds of formula (3) with corresponding linear alkyl epoxides in a way substantially similar to that described above for the preparation of the compound (7). Conditions for the reaction of a compound of formula (3) with volatile epoxides such as propylene oxide and ethylene oxide, include conducting the reaction under pressure.

Co-polymer preparation from the monomers of formulae (3), (4), (5), and (5a) and one or more compounds selected from polyhydric alcohols, di and tri-carboxylic acids, hydroxyacids, and cyclic esters can be accomplished by using one or more of the catalysts and conditions described above for the preparation of homopolymers comprising the repeating unit of formula (1a). The resulting co-polymers can be terminated with either hydroxyls or esterified carboxyls. Polymers can be linear, branched, star-shaped, or cross-linked, and can be random co-polymers, block copolymers, graft copolymers, or any combination thereof.

Of particular interest and utility are the hydroxyl terminated polymers and co-polymers comprising the repeating units of formula (1a). Such compounds have been found to be useful for making polyurethane polymers with widely varying properties.

Many polyurethane polymers and methods of their preparation are known in the art. Polyurethane polymers are compounds of exceptional industrial utility; they find numerous applications because the final properties of the resulting polymer can be influenced greatly through selection of active hydrogen monomers (typically, polyhydroxyl compounds) and isocyanates used, and by selecting the conditions used to prepare the finished polymer products.

Many of the polymers comprising the repeating unit of formula (6) are useful for making polyurethane polymers. For use in polyurethane synthesis, a polymer comprising the repeating unit of formula (6) can be prepared in a hydroxyl-terminated form, wherein two or more hydroxyl groups are present on average per representative polymer structure. This is typically accomplished by carrying out the polymerization reaction with at least one monomer selected from the stereoisomers of compounds of formula (3), (4), (5), and (5a) in the presence a sufficient amount of a co-polymer polyhydric alcohol having two or more hydroxyl groups, so that polymerization product has preferably an average molecular weight in excess of 500 Da, more preferably, in excess of 1000 Da, and has two or more hydroxyl groups, The resulting polymerization product comprising the unit of formula (6) can be a linear, branched, cross-linked, or star-shaped polymer. One or more of such polymerization product comprising the unit of formula (6) can then be used as polyol compounds in a reaction with one or more isocyanate compounds having two or more isocyanate groups. Many suitable isocyanate compounds are known in the art of polyurethane synthesis. Non-limiting examples of isocyanate compounds include diisocyanate compounds such as tolylene diisocyanate isomers, hexamethylene diisocyanate, pentamethylene diisocyanate, isophorone diisocyanate, 4,4'-methylenebis(phenyl isocyanate), and the like. Further non-limiting examples of isocyanate compounds include polyisocyanate compounds, and can be obtained by reacting one of the above diisocyanate compounds with a polyhydric alcohol or a polyhydric amine. Non-limiting examples of suitable polyisocyanate compounds also include adducts of one or more diisocyanate compounds obtained by reacting one or more of the polyhydric products comprising the repeating unit of formula (6) under conditions sufficient to cause reaction between the hydroxyl group and an isocyanate group. It has been found that such polyisocyanate compounds can be obtained by mixing appropriate quantities of various aliphatic and/or aromatic diisocyanate-compounds with a polyhydric alcohol comprising the repeating units of formula (6), and causing reaction to occur by means of heating and/or with catalysts sufficient to accelerate the reaction. Non-limiting examples of typical catalysts suitable for making the polyisocyanate compounds include dibutyl tin dilaurate, 1,4-diazabicyclo [2.2.2]octane (DABCO™, TED), and the like. The reaction of making a polyisocyanate compound from a polyhydric alcohol comprising the units of formula (6) can be carried out in the presence of an inert solvent, which may optionally be removed at the end of the reaction by distillation.

One or more of the polyhydric alcohols comprising a repeating unit of formula (6) can then be reacted with one or more isocyanate compounds having two or more isocyanate groups per representative molecule, thereby providing for a polyurethane polymer comprising one or more units of formula (6) per representative polymer molecule.

Such reactions occur readily under conditions typically known to those in the art of polyurethane synthesis, and include use of one or more catalysts known in the art and/or elevated temperatures. Non-limiting representative examples of typical catalysts include dibutyl tin dilaurate and DABCO. Elevated temperatures expedite formation of the desired polyurethane polymer, and typically, temperatures between 30 and 160° C. are sufficient to commence and accelerate the reaction. The reaction can be conducted at temperatures outside of the specified range, however, at lower temperatures, the reactions may be quite slow, while at higher temperatures, side reactions and partial polymer decomposition may occur. In general, preparation of polyurethane polymers comprising repeat units of formula (6) is an exothermic reaction and is successful without additional heating. Synthesis of polyurethane polymer comprising units of formula (6) is preferably carried out under substantially anhydrous conditions. If small quantities of water are present, the product is typically a foam polymer comprising both urethane and urea linkages. If a foam polymer is desired, the reaction is carried out using one more inert propellant compounds known in the art.

Various polyurethane polymers comprising units of formula (6) can thus be prepared and used to manufacture a plethora of polyurethane goods that in a way substantially similar to polyurethane polymers known in the art. Polyurethane polymers comprising the units of formula (6) can be solid or viscous liquids, rigid or flexible, and they can be prepared as thermoset or thermoplastic polymers. Depending on the specific polymer composition, they can be cast, extruded, or otherwise shaped in a variety of forms needed to manufacture finished polymer goods. The polyurethane polymers comprising units of formula (6) can contain various additives known in the art, such organic or inorganic fillers, pigments, stabilizers, anti-oxidants, and lubricants The polyurethane polymers disclosed herein are made with use of low-cost renewable monomers to provide the predominant part of the weight of the resulting polymers, thereby offering a cost advantage when compared to the known in the art polyurethanes made predominantly or exclusively with use of non-renewable petroleum- or coal-derived monomers.

The polyurethane polymers comprising units of formula (6) are also recyclable at the monomer level. If so desired, at the end of their useful life, the polyurethane polymers comprising the units of formula (6) can be treated by a transesterification reaction, to allow for the decomposition of the polymers and the formation of one or more monomers of formulae (3), (4), (5), and (5a), which can be recovered, purified and re-used.

EXAMPLES

Example 1

36 g of levulinic acid of 98% purity, 28 g of glycerol of 99% purity, 0.08 ml of concentrated sulfuric acid, and 60 ml of n-heptane were stirred in a round bottom flask equipped with a Dean-Starks adapter. The whole was brought to reflux by means of heating in an oil bath, and was refluxed for approximately 36 hours or until about 11 ml of water was collected in the trap of the adapter. The reaction mixture was neutralized by the addition of 0.2 g of calcium carbonate. The heptane was removed, and reaction mixture cooled, yielding approximately 53.2 g of a very viscous, pale-brownish, honey-like polymeric adduct that comprised compounds having structural repeating units of formula (1).

Example 2

20.3 g of the polymeric adduct prepared in Example 1 was dissolved in 80 ml of methanol containing 0.4 g of sodium methoxide. The resulting solution was stirred at room temperature, allowing for small quantities of free glycerol to separate on the bottom and on the walls of the reaction flask. The solution was filtered through a fiberglass wool plug, neutralized by vigorous stirring for 30 min with 2 g of anhydrous potassium dihydrogen phosphate, diluted with 100 ml of methyl tert-butyl ether (MTBE), and dried over anhydrous sodium sulfate. The solution was then filtered. MTBE and excess methanol were removed under reduce pressure, yielding 23.1 g of clear, slightly yellowish, practically odorless liquid that was analyzed by gas chromatography-mass spectrometry (GC-MS). The liquid was found to contain about 15% methyl levulinate and about 82% of the stereoisomers of the compound having formula (14):

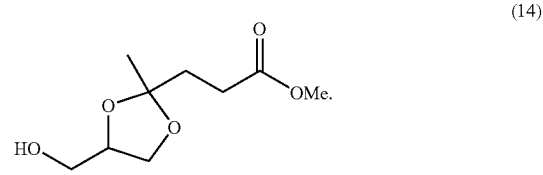

(14)

The stereoisomers of the compound of formula (14) were detected as two partially separable peaks on the GC chromatogram having approximately similar integration areas. The peaks had the following representative mass-spectra.

A mass-spectrum of one of the stereoisomers of the compound of formula (14) eluting with a retention time of approximately 15.06 minutes is shown in FIG. 1.

Figure 2:
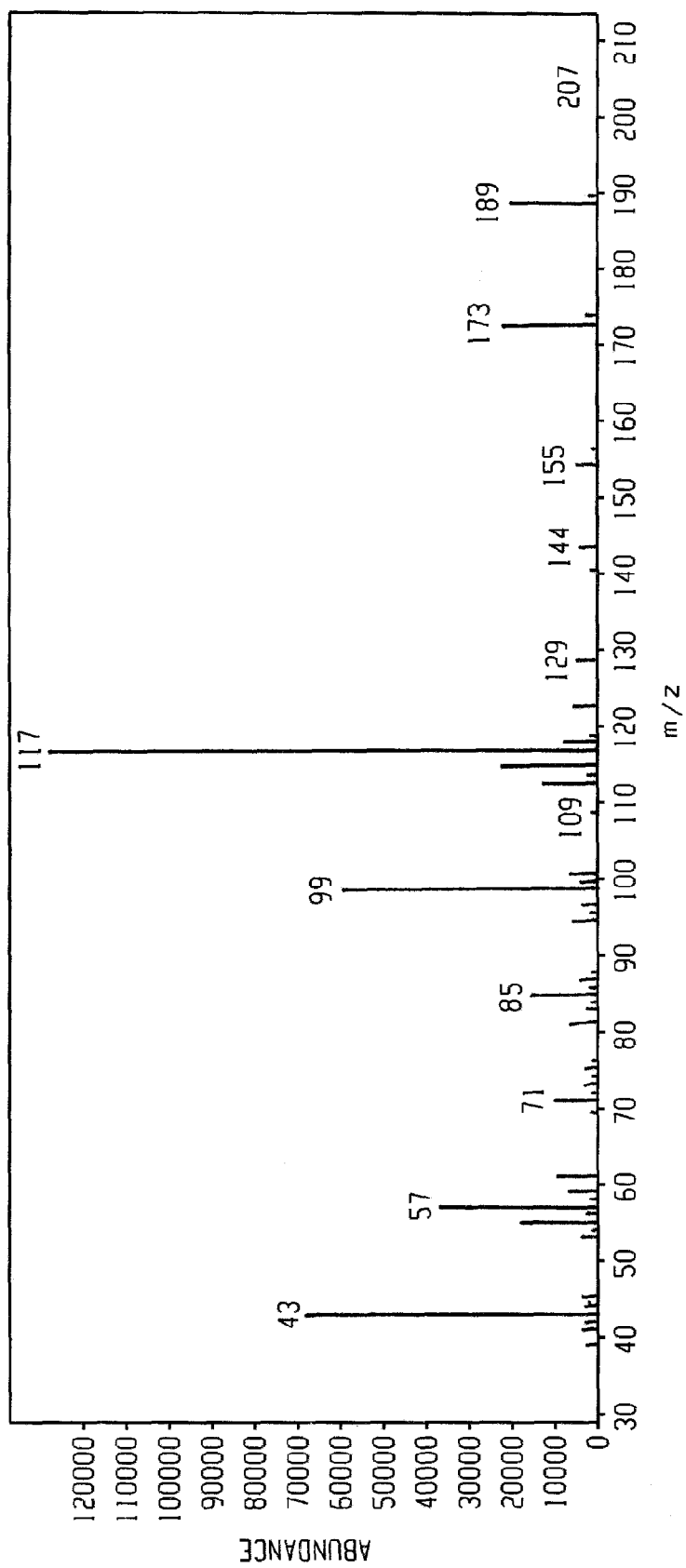
FIG. 2 is a mass spectrum of another stereoisomer prepared according to Example 2.

A mass-spectrum of another stereoisomer of the compound of formula (14) eluting with a retention time of approximately 15.24 minutes is shown in FIG. 2.

The resulting liquid mixture of products was also found to contain about 3% of the stereoisomers of diglyceryl ether levulinate ketals dimethyl esters of the formula (15):

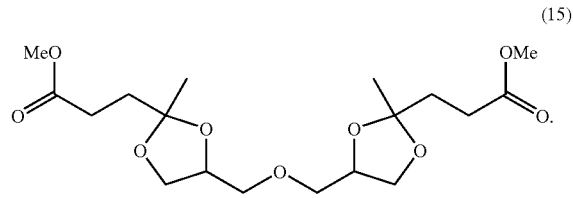

(15)

Example 3

5 g of the reaction product obtained in Example 1 were mixed with 20 ml of ethyl acetate and 0.2 g of potassium t-butoxide. The whole was stirred for about 45 min, and complete dissolution of the polymeric starting material was observed. The reaction mixture was neutralized by stirring with 2 g of anhydrous potassium dihydrogen phosphate for about 1 hr, dried over anhydrous sodium sulfate, filtered, and the excess ethyl acetate was evaporated under reduced pressure. The resulting oily, transparent, pale-yellowish liquid (6.2 g) was analyzed by GC-MS and was found to contain approximately 14% of ethyl levulinate, approximately 25% of hydroxyester isomers of formula (16):

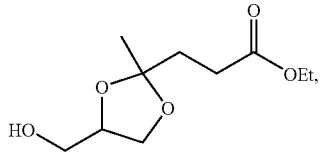
(16)

and approximately 55% of the stereoisomers of di-ester of formula (17).

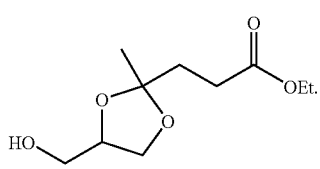
(17)

Small quantities of the stereoisomers of compound (18) were also present:

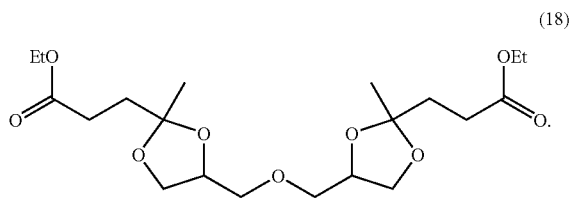
(18)

Example 4

Figure 3:
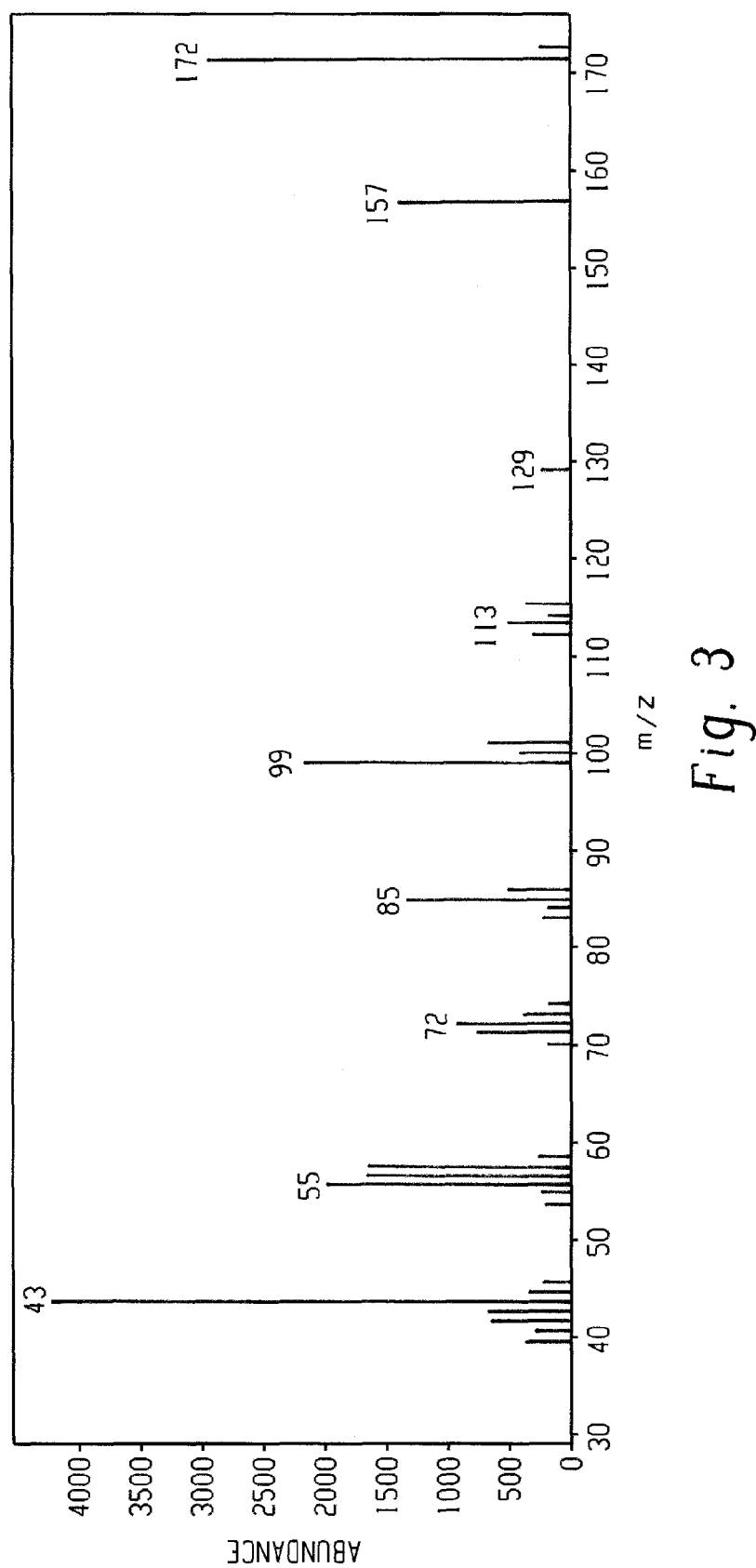
FIG. 3 is a mass spectrum of a lactone ketal prepared according to Example 4.

5 g of polymeric adduct prepared according to Example 11 and 0.2 g of potassium t-butoxide were stirred at 120-125° C. under vacuum (1 mm, 2 hr), and about 1 ml of clear distillate was collected. The distillate was analyzed by GC-MS and was found to contain predominantly the lactone ketal of formula (5). The compound of formula (5) had a representative electron ionization mass-spectrum shown in FIG. 3.

Example 5

10 ml of the hydroxyester of formula (14) obtained in Example 2 was heated with stirring under vacuum (6 mm, 80° C., 4 hours) until ethyl levulinate was substantially removed, as tested by GC-MS. The resulting liquid was mixed with 2 g of decene-1,2-oxide of 94% purity (Vicolox® 10 brand, Arkema Group), and a complete dissolution of epoxide was observed at room temperature. 0.025 ml of boron trifluoride diethyl etherate was introduced into the stirred reaction mixture and an exothermic reaction was observed with the temperature rising briefly to about 50° C. The reaction mixture was stirred for 20 min and an aliquot was taken for GC-MS analysis. The analysis showed complete conversion of the epoxide to several stereoisomers of the hydroxyester ketal compounds of formula (19a) and (19b).

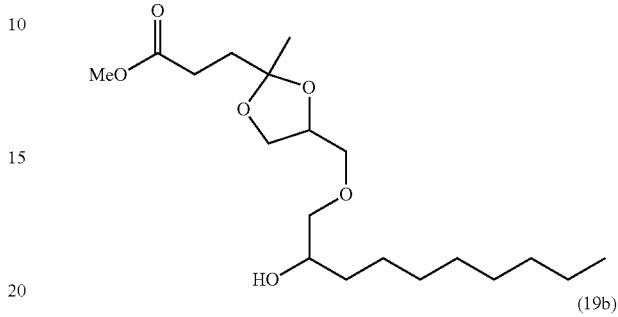
(19a)

(19b)

Example 6

The synthesis was carried out according to Example 5, except 2 g of octadecene-1,2-epoxide of 85% purity was used. The reaction products obtained had formulae (20a) and (20b):

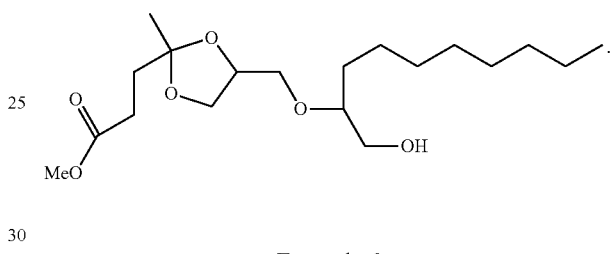
(20a)

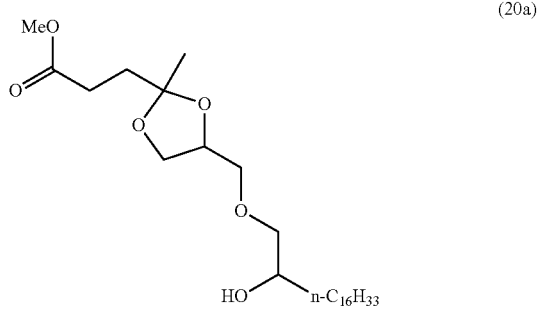
(20b)

Example 7-8

Excess solvent from the reaction mixtures of Examples 5 and 6 were evaporated under reduced pressure (0.5 mm, 150° C.) to give neat mixtures of compounds (19a), (19b) (Example 7) or compounds (20a), (20b) (Example 8). 10 ml of water was added to the resulting product mixtures, and the esters were saponified with slight excess of 0.1 N aqueous NaOH to give the corresponding sodium salts in aqueous solution. These solutions had emulsifying and surfactant properties that were not affected by the presence of 1 g/L calcium chloride or magnesium chloride.

Example 9

Levulinic acid (98% purity, 697.3 g), glycerol (99% purity, 554.2 g), concentrated sulfuric acid (0.25 g), and a stirring bar were placed in a weighted 2-liter round-bottom evaporating flask, and the whole was set to rotate at 10 rpm on a rotary evaporator equipped with an efficient vertical condenser cooled to 4° C., and a vacuum was applied using a vacuum pump capable of providing an eventual vacuum of 6 mm. The flask was rotated and heated using an oil bath with an initial temperature setting of 80° C. A rapid distillation of water was observed. After approximately 130 ml of water was collected in a receiving flask, the bath temperature was increased to 115° C., and distillation of water was continued until the rate of distillation had decreased to approximately less than 1 mL per 15 min. The bath temperature than was then increased to 150° C., and the reaction mixture was heated under a 0.2 mm vacuum for 1 hour. The reaction was then stopped, and the temperature of the reaction product was allowed to equilibrate to room temperature. The resulting polymerization product (1054.3 g) at room temperature was a viscous, slightly brownish, sticky, syrup-like liquid, and was practically insoluble in cold water.

The catalyst was then neutralized by adding 2 grams of dry sodium bicarbonate, and by stirring the content of the flask on a rotary evaporator at 100° C. for 2 hours, while a 6 mm vacuum was applied. The neutralized reaction product was allowed to cool to room temperature, and any insoluble inorganic matter was allowed to settle. The resulting viscous liquid co-polymer was stored at room temperature, and was used in subsequent examples in a decanted or filtered form.

The resulting product was predominantly a polymer comprising the repeating unit of formula (1).

Example 10

Levulinic acid (98% purity, 696.1 g), glycerol (99.5% purity, 607.5 g), concentrated sulfuric acid (1.0 g), and a stirring bar were placed in a weighted 2-liter round-bottom evaporating flask, and the whole was set to rotate at 100 rpm on a rotary evaporator equipped with an efficient vertical condenser cooled at 4° C., and a vacuum was applied using a vacuum pump capable of providing an eventual vacuum of 6 mm. The flask was rotated and heated using an oil bath with an initial temperature setting of 80° C. A rapid distillation of water was observed. After approximately 110 ml of water was collected in a receiving flask, the bath temperature was increased to 110° C., and distillation of water was continued until the rate of distillation had decreased to approximately less than 1 mL per 60 min (this took approximately 5 hours). The reaction was then stopped, and the temperature of the reaction product was allowed to equilibrate to room temperature. The resulting polymerization product (1087 g) at room temperature was a viscous, practically colorless, sticky syrup-like liquid sparingly soluble in cold water.

The resulting product was predominantly a polymer comprising the repeating unit of formula (1).

Example 11

Levulinic acid (98% purity, 700.1 g), glycerol (99.0% purity, 607.4 g), concentrated sulfuric acid (0.4 g), and a stirring bar were placed in a weighted 2-liter round-bottom evaporating flask, and the whole was set to rotate at 100 rpm on a rotary evaporator equipped with an efficient vertical condenser cooled at 4° C., and a vacuum was applied using a vacuum pump capable of providing an eventual vacuum of 6 mm. The flask was rotated and heated using an oil bath with an initial temperature setting of 80° C. A rapid distillation of water was observed. After approximately 130 ml of water was collected in a receiving flask, the bath temperature was increased to 105° C., and distillation of water was continued until it ahd practically subsided (approximately 6 hours). The reaction was then stopped, and the temperature of the reaction product was allowed to equilibrate to room temperature. The resulting polymerization product (1097 g) at room temperature was a viscous, practically colorless, sticky, syrup-like liquid sparingly soluble in cold water.

The resulting product was predominantly a polymer comprising the repeating unit of formula (1).

Example 12

A mixture 1.05 mol of triacetyl glycerol, 2.1 mol of glycerol, 1.96 mol of solketal, 2.65 mol of ethyl levulinate, 1.7 mol of levulinic acid, 0.4 mol of alpha-angelica lactone and 0.2 ml of concentrated sulfuric acid was magnetically stirred and heated under nitrogen to 100-105° C. in a round bottom flask equipped with a water-cooled condenser. Distillation of a mixture of acetone, ethanol, water, acetic acid and ethyl acetate was observed. Heating with stirring was continued until the distillation ahd practically subsided (about 16 hours). The resulting viscous, transparent, slightly yellowish liquid was poured into a 2 L evaporation flask, and the whole was heated on a rotary evaporator to 110-15° C. at a reduced pressure using a vacuum pump capable of providing an eventual vacuum of 6 mm. After distillation of the water and volatiles has subsided (approximately 6 hours), the resulting viscous polymerization product (939 g) was cooled down to room temperature.

The resulting product was predominantly a polymer comprising the repeating unit of formula (1).

Example 13

A mixture of 1.02 mol of glycerol, 2.95 mol of levulinic acid and 0.2 g of sulfuric acid was heated on a rotary evaporator to 80-90° C. at a reduced pressure a vacuum pump capable of providing an eventual vacuum of 6 mm, until distillation of water had practically subsided. The resulting product (385 g) was a mixture of ester products comprising predominantly trilevulinoyl glycerol and 1,2-dilevulinoyl glycerol.

Example 14

The synthesis was carried out according to Example 11, except that the starting reaction mixture additionally contained 40.2 grams of a mixture of glyceryl esters prepared according to example 13. The resulting product (1139 g) was a glycerol-branched polymer comprising the repeating unit of formula (1).

Example 15

The synthesis was carried out according to Example 14, except the added amount of ester prepared according to the Example 14 was 82.2 g. The resulting polymer (1226 g) was a glycerol-branched polymer comprising the repeating unit of formula (1).

Example 16

1021 g of the polymeric product comprising the repeating unit of formula (1) prepared according to Example 11 was slowly poured (over period of 1 hour) into a stirred reactor containing 1.2 liters of a methanolic solution containing 6 grams of sodium methoxide. After stirring at room temperature for 8 hours, the content of the reactor were collected, and the methanol was evaporated at reduced pressure using a rotary evaporator. The resulting yellowish-orange liquid was transferred to a separatory funnel and thoroughly mixed with 0.8 L of tert-butyl methyl ether. The contents were allowed to stand for 4 hours and separate into two layers. The lower level containing primarily glycerol, sodium salt of compound (3), wherein $R^3$ is H, and small quantities of sodium levulinate, was discarded, and the upper layer was stripped of the tert-butyl methyl ether using a rotary evaporator. The resulting slightly yellowish liquid (992 g) was analyzed by GC-MS and was found to contain approximately 12% of methyl levulinate, approximately 80% of the compound of formula (3), wherein $R^3$ is methyl, as a mixture of approximately equal amounts of cis- and trans-isomers, and small quantities of the compound of formula (5) and stereoisomers of compounds having formulae (21) and (22) (ca. 1% each):

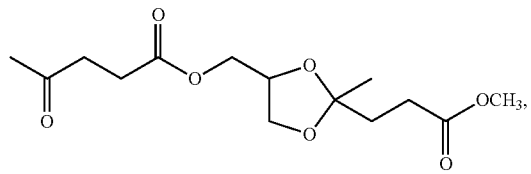

(21)

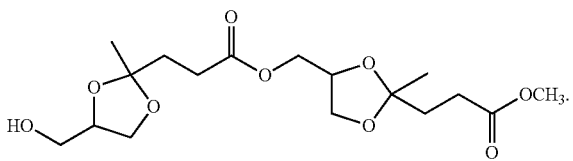

(22)

The resulting mixture of stereoisomers of compound of formula (3) was further purified by removal of methyl levulinate at a reduced pressure, and then further purified by distillation using a falling film column under 0.5-1 millibar vacuum and a temperature set at 130° C. The residual undistilled compounds 21 and 22 were collected and treated with methanol containing 0.2% sodium methoxide, to yield a 20:80 mixture of methyl levulinate and the compound of formula (3).

Example 17

The reaction was carried out according to Example 16, except that ethanol was used in the reaction instead of methanol, and the starting polymeric product (732 g) was prepared according to Example 12. The resulting product was analyzed by GC-MS and was found to contain approximately 9% of ethyl levulinate and 88% of the compound of formula (3), wherein $R^3$ is methyl, as a mixture of approximately equal amounts of cis- and trans-isomers. The compound of formula (3) was then further purified by distilling out ethyl levulinate at a reduced pressure.

Example 18

301.2 g of the polymer prepared according to Example 9 were stirred with 500 ml of n-butanol containing 6 grams of sodium hydroxide at room temperature for 24 hours. The resulting transparent yellowish solution was stripped of excess n-butanol on a rotary evaporator under reduced pressure, and the whole was mixed with 600 ml of n-heptane in a separatory funnel. The lower layer, containing primarily glycerol and sodium levulinate and the sodium salt of the compound of formula (3), wherein $R^3$ is H, was discarded, and the upper layer was filtered through a paper towel. The resulting practically colorless filtrate was stripped of heptane on a rotary evaporator, to yield a clear colorless liquid (385 g) that was analyzed by GC-MS. The liquid was found to contain approximately 24% butyl levulinate and approximately 73% of a 1:1 mixture of cis- and trans-isomers of the compound of formula (3), wherein $R^3$ is n-butyl.

The compound (3) was then further purified by distilling out butyl levulinate at a reduced pressure.

Example 19-23

5 grams of a 1.2:1 cis/trans isomer mixture of the compound of formula (3), prepared according to, Example 16, wherein $R^3$ is methyl, (96% pure, purified by distillation) were dissolved in 20 ml of each of the following:

(19) absolute ethanol with approximately 0.2% w/w sodium ethoxide,

(20) anhydrous n-butanol with approximately 0.2% W/W sodium n-butoxide,

(21) anhydrous isobutanol with approximately 0.4% sodium isobutoxide,

(22) anhydrous isoamyl alcohol with 0.3% sodium 3-methylbutoxide,

(23) 2-ethylhexyl alcohol with 0.3% sodium 2-ethylhexoxide.

The solutions were stirred for 12 hrs by means of magnetic stirring at room temperature (26° C.). Progression of the trans-esterification reaction was monitored by analyzing small aliquots of the reaction mixtures by GC-MS. Formation of esters of formula (3) was observed, wherein $R^3$ is ethyl (Example 19), n-butyl (Example 20), isobutyl (Example 21), isoamyl (Example 22), and 2-ethylhexyl (Example 23). The reaction did not result in any significant change of the cis/trans isomer ratio. After trans-esterification was complete, the reaction mixtures were neutralized by stirring for 8 hours with finely powdered potassium dihydrogen phosphate, and filtered. Excess alcohol was distilled from each sample under reduced pressure, thereby yielding the compounds of formula (3) in neat form as viscous liquids. The neat compounds were 94-97% pure (as mixtures of cis/trans isomers).

Example 24

2309 g of the compound of formula (3), $R^3$=$CH_3$, a 1.05:1 mixture of cis/trans isomers, purified by distillation under reduced pressure to a purity of about 97%, were fed to a falling film distillation column at a rate of about 90 grams per hour. The distillation column was maintained at 0.5-0.8 millibar vacuum, and the hot finger was maintained at 130° C. 780 g of the distillate was collected, and the distillate was found to contain a 1.55:1 mixture of cis/trans isomers of the compound (3). The undistilled material that passed through the column (1508 g) was found to contain a 0.81:1 mixture of cis/trans isomers of the compound of formula (3). The procedure was repeated several times separately with the mixtures containing either predominantly cis- or predominantly trans-isomers. After 5 distillations, a sample containing 180 grams of 93% pure cis isomer of the compound of formula (3) was obtained, a sample containing 226 grams of 88% cis isomer of the compound of formula (3) was obtained, and the remainder of material was divided in several fractions contained cis/trans isomers in ratios ranging from 82:18 to 24:76. The hydroxyesters prepared in this example were practically pure (over 99.5%) and contained no appreciable quantities of glycerol, methyl levulinate, or oligomers comprising the repeating units of formula (6).

Example 25

Sodium methoxide (0.1 g) was dissolved in 51 grams of the compound of formula (3) ($R^3$=$CH_3$, a 1.05: 1 mixture of cis/trans isomers, 99.7% pure), and was placed in a round bottom-flask equipped with magnetic stirring, a vertical air-cooled condenser, an adapter with a side arm, and with a flask to collect distilling methanol. The whole was stirred and heated to 180-200° C. under nitrogen at atmospheric pressure until distillation of methanol was no longer noticeable (approximately 2 hours). The reaction mixture rapidly became very viscous. The resulting melted polymer (approximately 41 grams) was poured out of the flask into a beaker and was allowed to cool. The polymeric product formed was a viscoelastic thermoplastic ketal-ester polymer comprising repeating units of formula (6) with a melting point to 65-70° C.; it had a considerable brown discoloration.

Example 26

The polymer synthesis was carried out according to Example 25, except 0.08 g of titanium (IV) isopropoxide was used instead of sodium methoxide, and the reaction was carried out at 220-240° C. for 3 hours. The content of the flask became viscous. A small polymer specimen was drawn from the flask, cooled and triturated with t-butyl methyl ether to determine the presence of starting monomer and any oligomers by GC-MS analysis. The polymer was practically insoluble in this solvent. The solvent extract was found to contain small quantities of compounds (5), (5a), (21), and a trace of the stereoisomers of acyclic oligomers of formula (23):

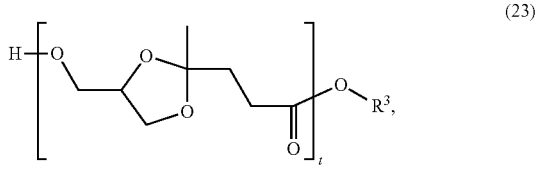

wherein t is an integer having value from 2 to 4, and $R^3$ is methyl.

Next, a 6 mm vacuum was applied, and the temperature was raised to 260-280° C. for about 1 hour. The reaction mixture was allowed to cool to about 140° C. under vacuum, and then about 24 grams of the molten polymer was poured out of the flask into a beaker. The resulting product was a transparent, practically colorless, viscoelastic thermoplastic polymer comprising repeating units of formula (6). The polymer had a melting point in the range of 70-75° C. The polymer remaining in the flask (15 g) was used in the subsequent examples.

Example 27

Example 27A

The polymer synthesis was carried out according to Example 25, except that 46 g of the compound of formula (3) having a cis/trans isomer ratio of 12:88 was used. The resulting product (36 g) was a transparent, practically colorless, viscoelastic, thermoplastic polymer comprising repeating units of formula (6). It had a melting point in the range of 85-90° C.

Example 27B

The polymer synthesis was carried out according to Example 25, except that 41 g of the compound of formula (3) having a cis/trans isomer ratio of 92:8. The resulting product (29 g) was a transparent, practically colorless, viscoelastic, thermoplastic polymer comprising repeating units of formula (6). It had a melting point in the range of 90-95° C.

Example 28

The polymer synthesis was carried out according to Example 25, except that 44 g of the compound of formula (3) having a cis/trans isomer ratio of 52:48, wherein $R^3$ is n-butyl was used. The resulting product (26 g) was a transparent practically colorless viscoelastic thermoplastic polymer comprising repeating units of formula (6). It had a melting point in the range of 72-77° C.

Example 29

15 g of the polymer prepared in Example 24 were heated in a round bottom flask equipped with a magnetic stirrer, a short-path distillation head, and a receiving flask in an oil bath maintained at 280-300° C. under vacuum using a pump capable of providing an eventual vacuum of 0.08 mm. A distillation of clear transparent liquid was observed, and approximately 6.2 g of distillate was collected in the receiving flask cooled by means of an ice bath. The liquid was analyzed by GC-MS and was found to contain approximately 62% of the compound of formula (5) and approximately 34% of the compound of formula (5a).

Figure 4:
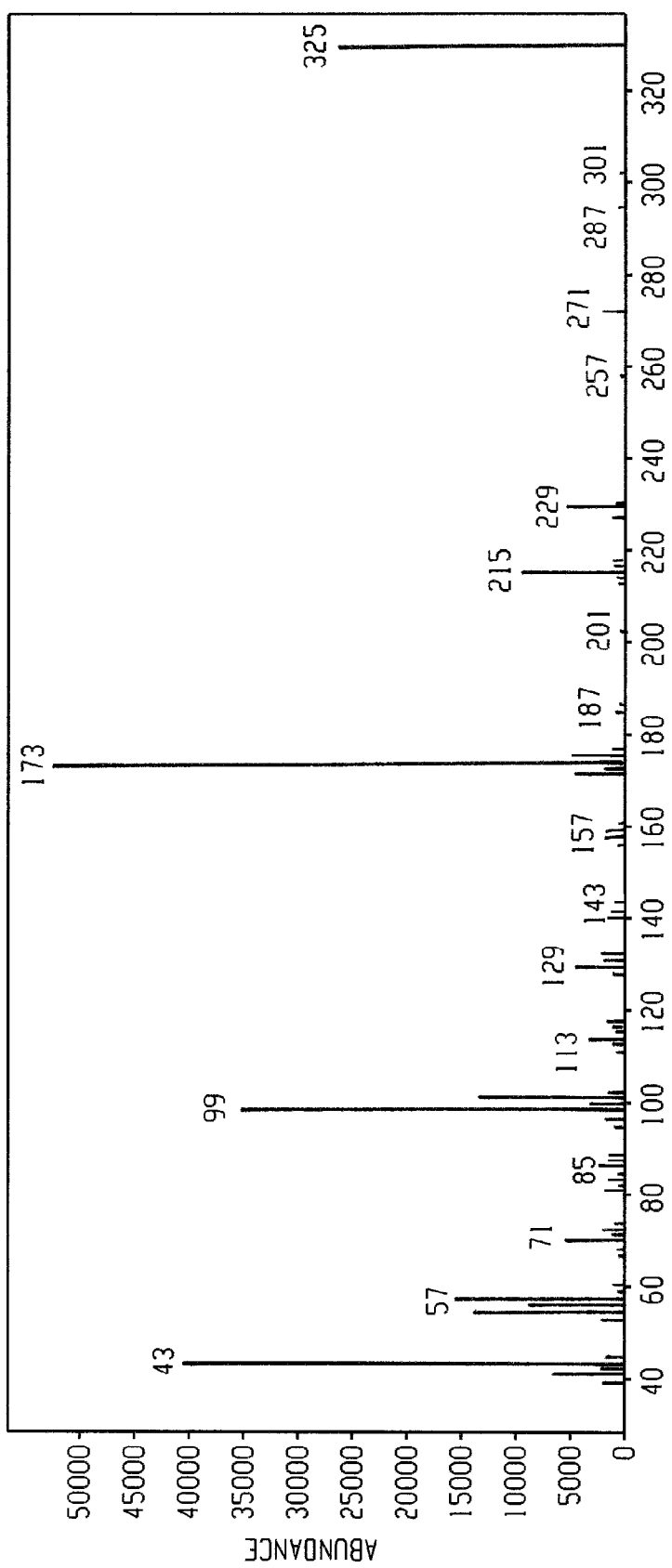
FIG. 4 is a mass spectrum of a compound prepared according to Example 29.

The compound of formula (5a) had a representative electron ionization mass-spectrum shown in FIG. 4.

The polymer remaining in the flask was trans-esterified with 20 ml of methanol containing 0.2% of sodium methoxide. The methanolic solution was analyzed by GC-MS were found to contain a 98% pure sample of the compound of formula (3), $R^3$=$CH_3$, with the ratio of cis-/trans-isomers of approximately 22:78.

Example 30

130.6 g of polymer repeating units of formula (6) prepared according to conditions described in Example 25 were placed in a round-bottom flask and 0.3 g of tin (II) 2-ethylhexanoate catalyst were added. The flasks was equipped with a magnetic stirrer, purged with nitrogen, and was heated to approximately 160° C. to melt the content and dissolve the catalyst. Vacuum was applied using a pump capable of providing an eventual vacuum of 0.1 mm, and the temperature of the flask was increased to approximately 280-300° C. Distillation of a clear, slightly yellowish liquid was observed, and the distillate (58 g) was collected in a receiving flask cooled by means of ice bath.

The distillate was cooled and analyzed by GC-MS and was found to contain approximately 57% of the compound of formula (5a) and 40% of the compound of formula (5a). 46 grams of the resulting mixture of compounds were separated by distillation under reduced pressure using a Kugelrohr-type apparatus providing a fraction containing 22 grams of 96% pure compound of formula (5), and a fraction containing 14 grams of 94% pure compound of formula (5a). Both compounds were obtained as colorless, practically odorless liquids that solidified to waxy solids on prolonged standing.

The polymer remaining in the flask was trans-esterified with methanol containing 0.2% of sodium methoxide. The methanolic solution was analyzed by GC-MS and were found to contain a 96% pure the compound of formula (3), $R^3=CH_3$, with the ratio of cis-/trans-isomers of approximately 19:81.

Examples 31-32

2 grams of one of the compound of formula (5) or the compound of formula (5a) were each dissolved in 10 mL of methanol containing 0.5% sodium methoxide, and the solution was stirred for 20 min at room temperature. The resulting solutions were each analyzed by GC-MS and were found to contain a practically pure (over 99%) cis-isomer of the compound of formula (3b), $R^3=CH_3$.

Example 33

8.6 grams of the compound of formula (5) prepared according to Example 30 and 0.03 g of tin (II) 2-ethylhexanoate were heated to 180-220° C., with stirring under nitrogen. The content of the reaction mixture had become viscous, and after 45 min the reaction was stopped and the content of the flask was cooled to room temperature. The resulting product was a polymer (8.3 g) comprising repeating units of formula (6) predominantly having a cis configuration. The polymer was a transparent, practically colorless, viscoelastic, thermoplastic polymer, with a melting temperature in the range of 95-100° C.

Examples 34-49

Linear and branched co-polymers comprising repeating units of formula (6) and having two or more ends of the polymer chains terminated with hydroxyl groups were prepared by co-polymerizing 0.1 mol of 99.4% pure compound of formula (3) ($R^3=CH_3$, 51:49 mixture of cis/trans isomers) and one of the following:
- (34) 0.011 mol of 1,1,1-tris(hydroxymethyl)ethane,
- (35) 0.006 mol of 1,1,1-tris(hydroxymethyl)ethane,
- (36) 0.010 mol of 1,1,1-tris(hydroxymethyl)propane,
- (37) 0.008 mol of pentaerythritol,
- (39) 0.006 mol of glycerol,
- (40) 0.002 mol of sorbitol,
- (41) 0.003 mol of xylitol,
- (42) 0.006 mol of erythritol,
- (43) 0.09 mol of 1,4-butane diol,
- (44) 0.012 mol of diethylene glycol,
- (45) 0.013 mol of 1,3-propanediol,
- (46) 0.015 mol of neopentyl glycol,
- (47) 0.02 mol of polyethylene glycol of average mol. weight of 1,200 Da,
- (48) same as Example 34, plus 0.001 mol of dimethyl adipate,
- (49) same as Example 37, plus 0.002 mol of dimethyl terephthalate.

The polymerization reactions were carried out in round bottom flasks equipped with a vertical condenser and a distillation head with side arm attached to a receiving flask. All reactions were carried out in the presence of titanium isopropylate (50 mg) as a catalyst, under nitrogen, by stirring and heating the reaction mixtures in an oil bath maintained at 220-230° C. for about 3 hours (until distillation of methanol practically subsided). After that, the bath temperature was reduced to about 160° C., and the reaction mixtures were stirred for 1 hr under vacuum using a pump capable of providing an eventual vacuum of 6 mm. The resulting viscous, transparent, practically colorless liquids were cooled to room temperature and stored for subsequent use. The amounts of polymers obtained were commensurate with the calculated (theoretical) loss of methanol and no more than an additional 4% weight loss. The prepared polymers were very viscous liquids at room temperatures.

The resulting polymers were linear co-polymers (Examples 43-47) or branched co-polymers (Examples 34-42, 48, and 49). The co-polymers comprising repeating units of formula (6) had two or more ends of the polymer chains terminated with hydroxyl groups.

Example 50

10.1 grams of polymer comprising repeating units of formula (1), prepared according to Example 9, 3.0 grams of isophorone diisocyanate, and 0.032 grams of dibutyl tin dilaurate were thoroughly mixed together in a dry box, using a glass stirring rod, at room temperature. The viscosity of the resulting solution gradually increased. The reaction mixture was then heated to 130° C. for 30 min, with occasional stirring using a glass stirring rod, and formation of a viscous, thermoplastic, practically colorless, transparent polymer was observed. The resulting polymer mass was then cooled to room temperature and solidified. The resulting polyurethane polymer comprising repeating units of formula (1) was a rigid practically transparent polymer with weak cold flow properties. At temperatures below 15° C., it was brittle. The polymer had a melting point in 90-95° C. range and was amenable to melt processing and extrusion. No significant deterioration in polymer properties were observed after 4 melt/cool cycles. The polymer was insoluble in water and practically insoluble in the ordinary organic solvents such as hydrocarbons, ethers, or alcohols.

Example 51

The synthesis was carried out according to Example 50, except that the quantity of isophorone diisocyanate was increased to 1.78 g. The resulting polymer at room temperature was a viscous transparent, adhesive-like thermoplastic product with good adhesion properties to paper, aluminum foil and low-energy surfaces such as polyethylene and polypropylene. The polymer was practically insoluble in water.

Example 52

The synthesis of polyurethane polymer was carried out according to Example 50, except that 1.42 g of hexamethylene 1,6-diisocyanate was used instead of isophorone diisocyanate. The resulting hot polymer was allowed to cool to room temperature, and to stay in open air for 24 hours. The product obtained by such a method was a flexible foam. It was a fully cured polyurethane polymer comprising repeating units of formula (1), and its properties did not change considerably over time. The polyurethane polymer was a practically colorless (off-white) thermoset polymer, and it could not be successfully re-processed by melt extrusion. The product was practically insoluble in water and in ordinary organic solvents such as hydrocarbons, ethers, or alcohols.

Example 53

The synthesis of polyurethane polymer was carried out according to Example 52, except that 1.46 g of tolylene diisocyanate (80:20 isomer mixture) was used instead of isophorone diisocyanate. The product was a rigid foam. It was a fully cured polyurethane polymer comprising repeating units of formula (1), and its properties did not change considerably over time. The polyurethane polymer was a yellowish thermoset polymer, which could not be successfully re-processed by melt extrusion. The product was practically insoluble in water and in ordinary organic solvents such as hydrocarbons, ethers, or alcohols.

Example 53

The synthesis of polyurethane polymer was carried out according to the Example 52, except that 2.28 g of 4,4'-methylenebis(phenyl isocyanate) was used instead of tolylene diisocyanate. The product was a rigid foam similar in its properties and appearance to the product obtained in Example 52.

Example 54

7.02 grams of the branched hydroxyl terminated polymer prepared according to Example 34, 2.03 grams of hexamethylene 1,6-diisocyanate, and 0.03 g of DABCO were thoroughly mixed in a glass vial placed in a dry box. A rapid exothermic reaction was observed with the temperature of the reaction mixture briefly rising to 95-100° C. The content of the reaction mixture rapidly solidified (in less than 4 minutes) to a transparent, slightly brownish product having practically no inclusions of gas bubbles. The resulting polyurethane polymer comprising fragments of formula (6) was cooled down and retrieved from the vial by breaking the vial. The resulting polyurethane polymer was a highly cross-linked, viscoelastic polymer with memory properties. The resulting polymer was practically insoluble in water and in ordinary organic solvents such as hydrocarbons, ethers, or alcohols. The product was a thermoset polymer and it could not be re-processed by melt extrusion without deterioration in polymer properties.

Example 55

The synthesis was carried out according to Example 54, except that the 7.08 g of a branched hydroxyl-terminated polymer was used as a starting material, and was prepared according to the Example 48. The resulting polyurethane was very similar to the polymer obtained in Example 54, except it was a considerably more rigid rubbery polymer.

Example 56

5.8 g of 94% pure decene-1,2-oxide were dissolved in 20.8 g of compound of formula (3) ($R^3$=methyl, 99.5% purity, 51:49 cis/trans isomer mixture). The whole was stirred at room temperature, and 0.08 g of boron trifluoride diethyl etherate was introduced. An exothermic reaction was observed. The whole was stirred for 1 hour, and the reaction mixture was allowed to cool to room temperature. The liquid was analyzed by GC-MS and was found to contain a mixture of isomers of compounds of the compounds of formula (7), wherein one $R^7$ is n-octyl and $R^8$ is hydrogen, and $R^7$ is hydrogen and $R^8$ is n-octyl.

Examples 57-64

The reactions of Examples 56 were repeated using different epoxides, as follows:
(57) octadecene-1,2-oxide 8.1 g,
(58) hexadecene-1,2-oxide 8.2 g,
(59) tetradecene-1,2-oxide 5.2 g,
(60) dodecene-1,2-oxide 5.6 g,
(61) hexane-1,2-oxide 4.6 g,
(62) butane-1,2-oxide 4.8 g,
(63) propylene-1,2-oxide 3.6 g,
(64) ethylene oxide 2.2 g.

The reactions of Examples 63 and 64 were carried out in pressurized glass vessels, while the other reactions were carried out at atmospheric pressure. The reaction mixtures were analyzed by GC-MS and were found to contain compounds of formula (7) with combinations of $R^7$ and $R^8$ corresponding to the chain lengths of the starting epoxides, and the unreacted compound of formula (3).

Examples 65-73

10 g of each of the reaction mixtures obtained in Examples 56-64 were placed in round bottom flasks equipped with a magnetic stirrer, a condenser, and a distillation head with an adapter connected to a receiving flask. 0.08 g of titanium (IV) isopropoxide and 0.5 g of trimethylol propane was added to each of the flasks, and the solutions were heated under nitrogen using an oil bath set at 200-220° C. After distillation of methanol had practically subsided (about 3 hours), the bath temperature was decreased to 140-160° C., and the stirring was continued for 1 hour under vacuum using a pump capable of providing an eventual vacuum of 6 mm. A weight loss was observed that was commensurate with the theoretical loss of methanol due to a complete hydroxyester polymerization, as measured by the weight of the resulting polymer products. An additional weight loss was also observed, commensurate with presence of inert volatile impurities in the starting epoxides used in Examples 56-64. The resulting polymeric products were cooled to room temperature, purged with nitrogen and stored at room temperature. The polymeric products were highly viscous colorless or slightly yellowish transparent or semi-transparent liquids at room temperature. The polymeric products were branched hydroxyl-terminated random co-polymers comprising repeating units of formula (6) and repeating units of formula (24):

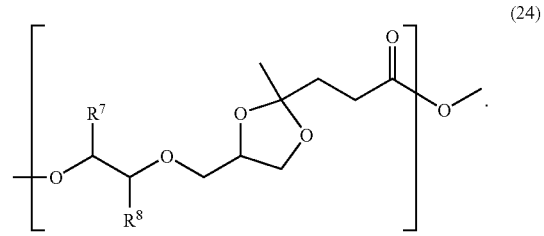

The co-polymeric hydroxyl-terminated compounds prepared in this example were found to be suitable for making rigid and flexible polyurethanes conditions substantially similar to those described in Examples 50-55.

Example 74

The reaction was carried out according to Example 56, except that the epoxide used was 10.2 g of a fully epoxidized soybean oil (Vicoflex® 7170, Arkema).

Example 75

506.2 grams of a fully epoxidized soybean oil (Vicoflex 7170 brand, Arkema) were mixed with 1 L of anhydrous methanolic solution containing 2.1 g of sodium methoxide, and the resulting mixture was magnetically stirred at room temperature (18° C.) for 6 hours. The progression of trans-esterification over time was followed by gas chromatography. After the trans-esterification reaction was found to be substantially complete, the reaction mixture was neutralized by the addition of 12.8 grams of finely powdered anhydrous potassium dihydrogen phosphate, followed by an additional stirring overnight (12 hours). The resulting mixture was filtered and the methanol was evaporated under reduced pressure using a rotary evaporator with a water bath set to 40° C. The resulting oil was dissolved in 1 L of hexanes, filtered, and the hexanes were removed under reduced pressure using a rotary evaporator. A clear transparent product with weak oily odor (485 g) was thereby obtained and was analyzed by GC-MS. When using a TIC integration method, the oil was found to contain approximately 9% methyl hexadecanoate, 5% methyl octadecanoate, 42% methyl 9,10-epoxy-9-octadecenoate, 40% isomers of methyl 9,10,-12,13-bisepoxy-9,12-octadecenoate, and small quantities of the esters of other saturated and epoxidized unsaturated fatty acids.

Example 76

The synthesis was carried out according to Example 56, except that the epoxide used was 8.2 g of the mixture of epoxidized unsaturated fatty acid esters prepared according to Example 75. The reaction mixture was analyzed by GC-MS and was found to comprise reaction products having formulae (9), (1.0a), (10b), unreacted the compound of formula (3), and the methyl esters of hexadecanoic and octadecanoic acid in quantities commensurate to their amounts in the starting material.

Example 77

0.4 g of the reaction product mixture obtained in Example 74 was trans-esterified by dissolving it in 4 ml of methanol containing 0.5% sodium methoxide, and the whole was stirred for 4 hr at room temperature. The reaction mixture was neutralized by stirring with powdered 0.32 g of anhydrous potassium dihydrogen phosphate for 1 hour, filtered and analyzed by GC-MS. The product mixture was found to be practically identical to the that obtained in Example 76.

Examples 78-79

10 g of one of the reaction product mixtures obtained in Examples 74 or 76 were treated according to the conditions of Examples 65-73. The resulting product was a cross-liked co-polymer containing repeating units of formula (1) and fragments derived from the modified fatty acid ester derivatives of formulae (9), (10a), and (10b). The resulting polymers were rubbery transparent thermoset elastomers with moderate yellow-orange discoloration. The polymers were practically insoluble in water, acetone, methylethylketone, hydrocarbons, ethers, and esters.

Approximately 0.2 g of each of the polymers obtained in this Example were de-polymerized by treatment according to the conditions described in Example 77. The GC-MS analysis of the resulting mixture of de-polymerized products showed that the mixture had a substantially similar composition to that observed in Examples 76 and 77, with the exception of the content of the methyl esters of hexadecanoic and octadecanoic acid, which was less than 2%.

Example 80

(a) The reaction was carried out according to Example 74 on a 5.4 fold scale. Powdered sodium fluoride (1 g) was added to neutralize the catalyst, and the whole was stirred for 18 hours at room temperature and filtered. The excess of compound (3) distilled out at reduced pressure, to give approximately 61 g of a modified triglyceride adduct having approximately 4.6 hydroxyl groups per molecule of triglyceride (a free-flowing transparent viscous liquid with moderate yellow-orange discoloration).

(b) 20.1 grams of this product were thoroughly mixed with 3.2 grams of hexamethylene-1,6-diisocyanate and 50 mg of dibutyl tin dilaurate, and the mixture was cured for 1 hour at 105° C. The resulting polyurethane polymer was a closed-cell, flexible, soft, fully cured yellow foam (thermoset polymer).

Example 81

(a) The modified triglyceride synthesis was carried out according to Example 80, except that addition of sodium fluoride was omitted. The resulting product was a partially cross-linked adduct with molecular weight of approximately 4500 Da.

(b) 19.3 grams of this product was thoroughly mixed with 1.3 grams of hexamethylene-1,6-diisocyanate and 50 mg of dibutyl tin dilaurate, and the mixture was cured for 1 hour at 105° C. The resulting polyurethane polymer was a closed-cell, flexible, soft, yellow, fully-cured foam (a thermoset polymer) with properties very similar to those obtained in Example 80.

Examples 82-83

The polyurethane foams obtained in Examples 80 and 81 were depolymerized according to Example 77. The resulting product mixture was found to be substantially similar to those observed in Examples 76 and 77, with the exception of the presence of the compound of formula (3) which was present in the products of the present Examples only in small quantities (2-3) %.

Example 84

5.1 g of branched hydroxyl-terminated co-polymer prepared according to Example 36 were dissolved in 8 g of tolylene diisocyanate (80:20 isomer mixture), and 0.02 g of dibutyl tin dilaurate was added. The whole was heated with vigorous stirring to 85-90° C. under nitrogen, and the excess tolylene diisocyanate was evaporated under reduced pressure. The resulting polymeric product (7.3 g) is an isocyanate-terminated branched polymer (a polyisocyanate) comprising repeating units of formula (6). The product was a viscous yellowish transparent liquid.

Examples 85-86

The synthesis of polyurethane foams was carried out according to Examples 80 and 81, except that the synthesis was carried out with 2.6 g of the polyisocyanate polymer obtained in Example 84, instead of hexamethylene diisocyanate. The resulting polyurethane foams were similar in their properties to the foams obtained in Examples 80 and 81, except they were more rigid.

Examples 87-88

One of the following:
(Example 87) 15.6 grams of the modified triglyceride prepared according to Example 80(a), or
(Example 88) 15.1 grams of the fatty ester adduct prepared according to Example 76, followed by distillation of excess compound of formula (3), was refluxed in 100 ml of methanol containing 0.05% of p-toluene sulfonic acid, to effect a transesterification reaction. The solution was monitored by GC-MS for appearance of methyl levulinate and methyl 4,4-dimethoxypentanoate. After the reaction was deemed complete (about 6 hours), both solutions were neutralized with 100 mg of sodium bicarbonate, filtered, and stripped of methanol under reduced pressure, to give a mixture of 1-glyceryl ether modified fatty acid esters (as oily liquids).

The glyceryl ether adducts were then mixed with 0.2 g of titanium isopropylate and heated to 95-100° C. under 6 mm vacuum, with stirring, until the content had become viscous (about 3 hrs), to give highly branched or crosslinked polyester-polyether compounds having molecular weights of approximately 3,500 Da.

5 gram portions of each of the resulting cross-linked polymers were mixed with 0.5 ml of methylethylketone and 0.3 grams of tolylene diisocyanate, and 0.01 g of dibutyl tin dilaurate was added. The mixtures were each stirred thoroughly and placed in a vacuum oven set at 100° C., incubated at atmospheric pressure for about 15 min, and then a vacuum was applied using a pump capable of providing an eventual 6 mm vacuum. The reaction mixtures were then left at 6 mm vacuum at 100° C. for 2 hrs, and then cooled down and brought to atmospheric pressure. The resulting polyurethanes were propellant-expanded, semi-rigid foams with density of about 0.22 g per cm$^3$.

Example 89

30 grams of a cellulose acetate polymer with 39.8% acetyl content and $M_n$ ca. 30,000 (Sigma-Aldrich Cat. No. 18, 095-5) were mixed with 50 grams of the compound of formula (3) ($R^3$=methyl, 99.5% purity, 51/49 cis/trans mixture of isomers), and 0.2 grams of titanium isopropylate was added. The whole was stirred and heated to 160-180° C. for 6 hours under nitrogen at atmospheric pressure, and then under 1 mm vacuum, to remove any unreacted compound of formula (3). The resulting polymer (42g) was a water-insoluble polyhydroxylated graft polymer with a cellulose polymer backbone and pendant groups comprising repeating units of formula (6). The polymer was a transparent, agar-like gel practically insoluble in water.

Example 90

Reaction product mixtures comprising epoxide adducts prepared in Examples 56-67 and 76 were each stripped of the excess of hydroxyester compound of formula (3) by distillation under reduced pressure. 3.2-3.3 grams of each of the resulting products were saponified with 0 ml of 1 M sodium hydroxide by vigorous stirring for 2 hrs at 85-90° C. Excess base was neutralized by titration with aqueous hydrochloric acid to pH 8-9, and the solutions were diluted with water to a final volume of 15 ml. The solutions of sodium salts of the saponified adducts of the compound of formula (3) with the various epoxides were then examined for their surfactant properties using a 1:1 hexane-water emulsion forming test, and by evaluating the stability of such emulsions in the presence and in the absence of calcium or magnesium ions (final concentrations of 1% $CaCl_2$ or 1% $MgCl_2$ were used in the emulsion tests). In addition, the saponified compounds were also tested in hexane-water emulsion tests at pH 3, and non-saponified compounds were also tested for their surfactant properties at pH 7. All emulsion tests were performed at room temperature.

Salts of the compounds obtained by saponification of the epoxide adducts of Example 76 and of Examples 56-60 were found to be good surfactants capable of forming and supporting stable hexane-water emulsions, and their surfactant properties were not adversely affected by the presence of calcium or magnesium ions. At acidic pH, the properties of the compounds Example 76 and Examples 56-60 were also found satisfactory. Non-saponified compounds of Examples 56-60 were found to be "water-in-oil" type emulsifiers.

Example 91

Plasticized polymer compositions and various blends of the polymeric compounds comprising fragment of formula (6) were prepared by a melt mixing and extrusion method, using one of the following polymers:
(a) PVC, poly(vinylchloride) powder (average $M_n$ ca. 55,000, average $M_w$ 97,000, inherent viscosity 0.92, relative viscosity 2.23, supplier Sigma-Aldrich Company, Cat. No. 34, 677-2),
(b) PHB, poly(3-hydroxybutyrate), (natural origin, Tm 172° C., supplied by Sigma-Aldrich Cat. No. 36, 350-2),
(c) AC, a cellulose acetate polymer with 39.8% acetyl content and $M_n$ ca. 30,000 (Sigma-Aldrich Cat. No. 18, 095-5),
(d) PLA (L-polylactide, inherent viscosity 0.90-1.20, Average $M_w$ 10,000-150,000, Tg 48.5° C., Supplied by Sigma-Aldrich Company, Cat. No. 53, 117-0).

Plasticized and blended compositions were prepared at a 5 g scale by pre-mixing cold ingredients. Each of the resulting mixtures were individually fed into a pre-cleaned, miniature twin-screw mixer-extruder chamber of a Daca Microcompounder (Daca Instruments) under nitrogen, with the mixing chamber heated to 5-10° C. above the melting temperature of the component with the highest melting point, and the motor speed was set to 100 rpm. The samples were mixed for about 5 minutes, and the resulting melt was then extruded out of the mixing chamber as a flexible rod (diameter 3 mm), which was immediately cooled to room temperature in ambient air.

The plasticizers and the polymer blends were tested at several concentrations including at least one compound of the present disclosure at 5, 10, 25, and 50% by weight of the resulting composition.

Glass transition temperature data (by differential scanning calorimetry), and plasticizer exudation data were collected using plasticized specimens cut from the extruded rods that have shown a satisfactory compatibility and acceptably low levels of exudation of the polymer composition components.

Polymer blends comprising one of PHB, PLA, and AC were found compatible in a broad concentration range with the polymeric compounds prepared in Examples 26-28, 33, 50; 51, 65-73, 89. Such blends were significantly plasticized, as displayed by significantly lowered glass transition points in comparison with non-plasticized PHB, PLA, and AC. The same compounds were also found to have limited compatibility with PVC (up to 10%), reducing the glass transition point of the plasticized PVC by about 15-30° C.

PHB, PLA, AC polymers were also successfully plasticized with compounds prepared in Examples 34-49, as well as with the compound of formula (5), (5a), and with the compound of formula (3) and (4), except cases wherein $R^3$ was H.

Among the compounds tested, the PVC polymer was most successfully plasticized with compounds prepared according to Examples 80(a), 81(a), 57-61, 76 (after removal of excess of compound 3 by distillation), compounds of formula 5a, and compounds of formula (3) and (4), wherein both $R^3$ and $R^6$ were $C_4$-$C_8$ linear or branched alkyls.

Example 92

2.1 grams of the polyurethane polymer comprising repeating units of formula (6) obtained in Example 52 were stirred at room-temperature in 15 ml of absolute ethanol containing 0.5% of sodium ethoxide until complete dissolution was observed (about 5 hours). The resulting solution was neutralized by stirring for 1 hour with powdered potassium dihydrogen phosphate, and the ethanol was distilled out under reduced pressure. The residue was dissolved in tert-butyl methyl ether and filtered. The filtrate was analyzed by GC-MS and was found to contain 95% pure compound of formula (3) ($R^3$=Et, cis/trans isomer mixture). The tert-butyl methyl ether was evaporated under reduced pressure, yielding about 1.52 g of the neat compound of formula (3).

Example 93

The reaction was carried out according to Example 92, except the polyurethane polymer was 2.3 grams of the polymer prepared in Example 54, and n-butanol with 0.3% of sodium n-butoxide was used. The resulting neat monomer (1.78 g) was a 97% pure compound of formula (3) ($R^3$=n-Bu, cis/trans isomer mixture).

A number of embodiments of the disclosure have been described. Nevertheless, it will be understood that various modifications may be made without departing from the spirit and scope of the disclosure. Accordingly, other embodiments are within the scope of the following claims.

What is claimed is:
1. A compound having the formula:

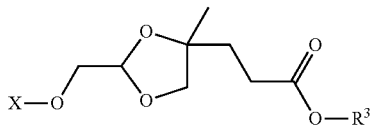

wherein $R^3$ is hydrogen; methyl; linear, branched, or cyclic alkyl; linear, branched, or cyclic alkenyl; aryl; aralkyl; and alkyloxyalkyl; and
X is selected from hydrogen, or

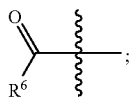

wherein $R^6$ is selected from hydrogen; linear, branched, or cyclic alkyl; linear, branched or cyclic alkenyl; aryl; aralkyl; oxoalkyl; and alkyloxyalkyl; or a salt thereof.

2. A compound having the formula:

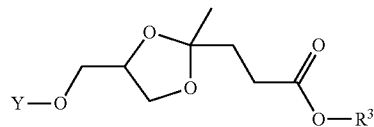

wherein $R^3$ is hydrogen; methyl; linear, branched or cyclic alkyl; or cyclic alkyl; linear, branched or cyclic alkenyl; aryl; aralkyl, or alkyloxyalkyl; and
Y is selected from the group comprising:

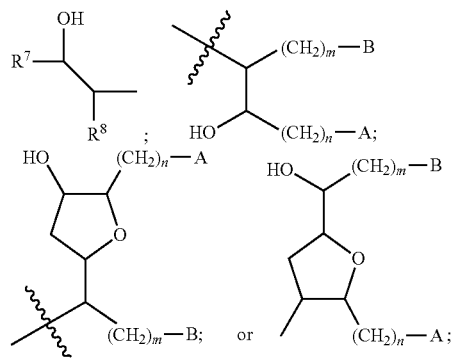

wherein one of $R^7$ or $R^8$ is hydrogen and the other is a $C_1$-$C_{30}$ linear alkyl, one of A or B is hydrogen and the other is an ester, and m and n are independently integers from 0 to 20, such that the sum of m+n=8 to 21; or a salt thereof.

3. The compound of claim 1, wherein $R^3$ is selected from a linear, branched, or cyclic alkyl; linear, branched, or cyclic alkenyl; aralkyl; and alkyloxyalkyl.

4. The compound of claim 2, wherein $R^3$ is selected from a $C_3$-$C_{30}$ linear, branched, or cyclic alkyl; linear, branched, or cyclic alkenyl; aralkyl; and alkyloxyalkyl.

5. The compound of claim 2, wherein one of $R^7$ or $R^8$ is a $C_6$-$C_{30}$ linear alkyl.

6. The compound of claim 4, wherein one of $R^7$ or $R^8$ is a $C_6$-$C_{14}$ linear alkyl.

7. The compound of claim 1, wherein the substituted oxymethylene moiety attached to the dioxolane ring is predominantly in the cis configuration relative to the configuration of the side chain bearing the carboxyl group.

8. The compound of claim 2, wherein the substituted oxymethylene moiety attached to the dioxolane ring is predominantly in the cis configuration relative to the configuration of the side chain bearing the carboxyl group.

9. The compound of claim 1, wherein the substituted oxymethylene moiety attached to the dioxolane ring is predominantly in the trans configuration relative to the configuration of the side chain bearing the carboxyl group.

10. The compound of claim 2, wherein the substituted oxymethylene moiety attached to the dioxolane ring is predominantly in the trans configuration relative to the configuration of the side chain bearing the carboxyl group.

11. The compound of claim 1 wherein the substituted oxymethylene moiety attached to the dioxolane ring is exclusively in the cis configuration relative to the configuration of the side chain bearing the carboxyl group.

12. The compound of claim 2 wherein the substituted oxymethylene moiety attached to the dioxolane ring is exclusively in the cis configuration relative to the configuration of the side chain bearing the carboxyl group.

13. The compound of claim 1 wherein the substituted oxymethylene moiety attached to the dioxolane ring is exclusively in the trans configuration relative to the configuration of the side chain bearing the carboxyl group.

14. The compound of claim 2 wherein the substituted oxymethylene moiety attached to the dioxolane ring is exclusively in the trans configuration relative to the configuration of the side chain bearing the carboxyl group.

15. The compound of claim 1, wherein $R^3$ is hydrogen.

16. The compound of claim 2, wherein $R^3$ is hydrogen.

17. The compound of claim 12, wherein the compound is the salt of an alkali metal, an alkaline-earth metal, ammonia, or an amine.

18. A method of preparing a compound having the formula:

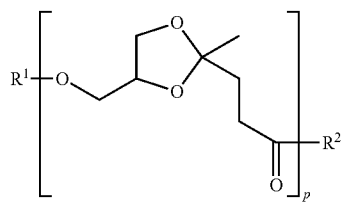

wherein
$R^1$ is hydrogen or a carbon atom of a levulinate fragment or a γ-valerolactone derivative;
$R^2$ is hydroxyl, an oxygen atom of glycerol, an oxygen atom of an esterified glycerol fragment, an oxygen atom of a diglyceryl fragment, or an acrolein fragment; and
p is an integer from 1 to 100;
the method comprising reacting glycerol or a compound having the formula:

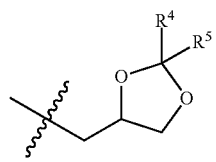

wherein
$R^4$ and $R^5$ are independently selected from the group comprising hydrogen; methyl; linear, branched or cyclic alkyl; linear, branched or cyclic alkenyl; aryl, and arylalkyl; or
a mono-, di-, or tri-ester of glycerol with a linear or branched alkanoic acid having one to six carbon atoms; or
a mixture of glycerol and a mono-, di-, or tri-ester of glycerol with a linear or branched alkanoic acid having one to six carbon atoms; or
a monolevulinate ester of glycerol;
with a levulinic derivative in the presence of an acid catalyst and under conditions sufficient for removal of water from the reaction mixture.

19. A method for preparing a compound of claim 1, the method comprising reacting a compound having the formula:

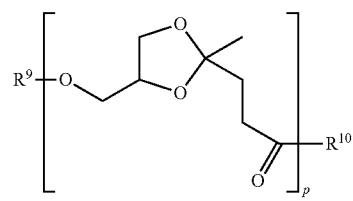

wherein:
$R^9$ is hydrogen or a carboxyl moiety;
$R^{10}$ is $OR^{11}$, or $N(R^{12})_2$;
$R^{11}$ and $R^{12}$ are independently hydrogen, methyl or a linear, branched, or cyclic alkyl; and
p is an integer;
with a monohydric alcohol or a carboxylic ester in the presence of a base catalyst.

20. A polymer comprising a unit having the formula:

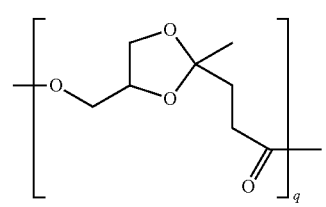

wherein q is an integer.

21. The polymer of claim 20 wherein the polymer comprises a polyurethane.

22. The polymer of claim 20 wherein the polymer comprises units derived from polymerization of a compound of formula:

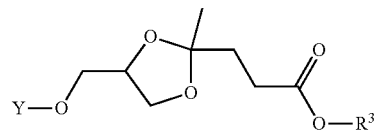

wherein $R^3$ is hydrogen; methyl; linear, branched or cyclic alkyl; or cyclic alkyl; linear, branched or cyclic alkenyl; aryl; aralkyl, or alkyloxyalkyl; and
Y is selected from the group comprising:

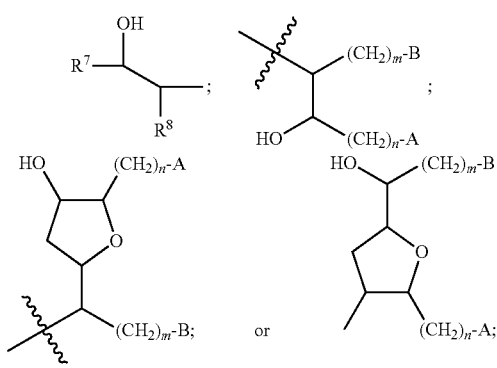

wherein one of $R^7$ or $R^8$ is hydrogen and the other is a $C_1$-$C_{30}$ linear alkyl, one of A or B is hydrogen and the other is an ester, and m and n are independently integers from 0 to 20, such that the sum of m+n=8 to 21; or a salt thereof.

23. A plasticized polymer composition comprising:
a) a base polymer; and
b) a compound of claim 1.

24. The plasticized polymer composition of claim 23, wherein the base polymer comprises vinyl chloride polymer, poly(3-hydroxyalkanoate) polymer, poly(lactate) polymer, or polysaccharide polymer.

25. The method of claim 18 wherein the levulinic derivative comprises a levulinic acid, levulinic ester, angelicalactone, or a dialkyl ketal of levulinic ester, or a mixture of two or more thereof.

26. The method of claim 25 wherein the mixture of two or more levulinic derivatives comprises about one molar equivalent of the mixture per molar equivalent of glycerol.

27. The method of claim 18, wherein $R^4$ and $R^5$ are not both hydrogen.

28. The method of claim 25, wherein the levulinic acid and glycerol have water content of 10% or less.

29. A compound having the structure:

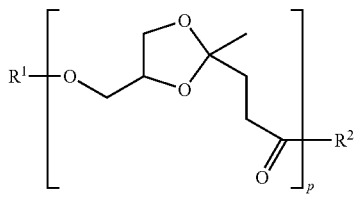

wherein
$R^1$ is hydrogen or a carbon atom of a levulinate fragment or a γ-valerolactone derivative;
$R^2$ is hydroxyl, an oxygen atom of glycerol, or an oxygen atom of an esterified glycerol fragment, an oxygen atom of a diglyceryl fragment, or an acrolein fragment; and
p is an integer from 1 to 100.

30. The method of claim 19 wherein the monohydric alcohol is in excess relative to the compound and the method further comprises removal of the excess monohydric alcohol by distillation.

31. The method of claim 19 wherein the base catalyst comprises an alkali or alkali-earth hydroxide or alkoxide.

32. The method of claim 19 wherein the method results in negligible traces of 1,3 glycerol ketals of esterified levulinate.

33. A compound having the formula:

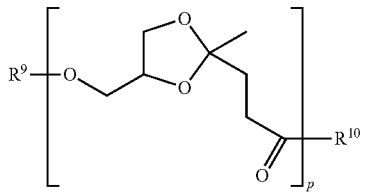

wherein
$R^9$ is hydrogen, methyl, or a carboxyl moiety;
$R^{10}$ is $OR^{11}$ or $N(R^{12})_2$;
$R^{11}$ is hydrogen, methyl, or a linear, branched, or cyclic alkyl; and $R^{12}$ is hydrogen, methyl, or a linear, branched, or cyclic alkyl; and
p is an integer.

34. The method of claim 18 wherein the reaction is carried out using glycerol and levulinic acid with water contents of about 10% or less.

35. A solution comprising a compound comprising one or more of the compounds:

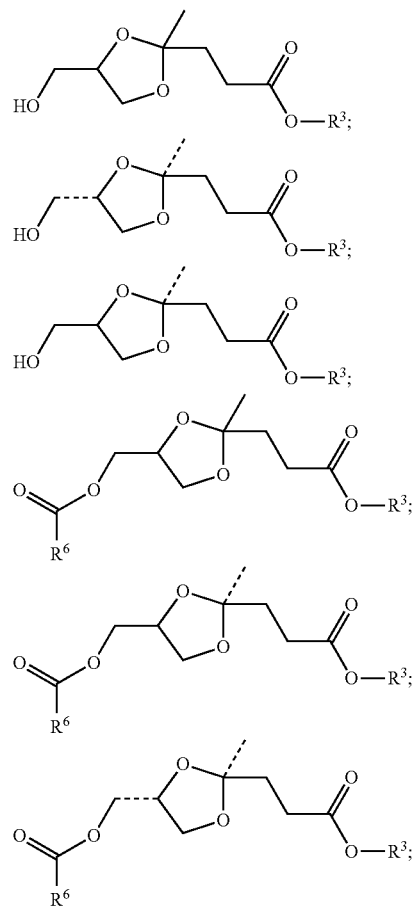

wherein
$R^3$ is hydrogen; methyl; linear, branched or cyclic alkyl; linear, branched or cyclic alkenyl; aryl, aralkyl, or alkyloxyalkyl; and
$R^6$ is hydrogen; methyl; linear, branched or cyclic alkyl; linear, branched or cyclic alkenyl; aryl; aralkyl; oxoalkyl; or alkyloxyalkyl, or a salt thereof.

36. The solution of claim 35 further comprising water, wherein $R^3$ is an alkyl group having one to five carbons.

37. A formulation comprising one or more of the compounds:

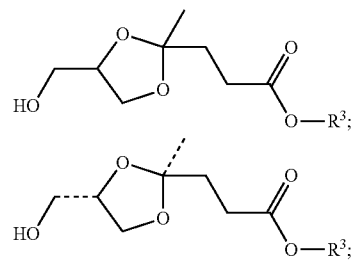

-continued

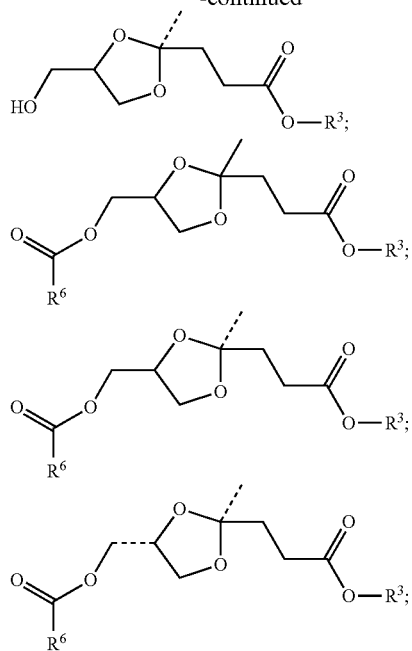

wherein
R³ is hydrogen; methyl; linear, branched or cyclic alkyl; linear, branched or cyclic alkenyl; aryl; aralkyl; or alkyloxyalkyl; and
R⁶ is hydrogen; methyl; linear, branched or cyclic alkyl; linear, branched or cyclic alkenyl; aryl; aralkyl; oxoalkyl; or alkyloxyalkyl, or a salt thereof.

38. The formulation of claim 37 wherein the formulation is a degreasing formulation, a paint thinning formulation, a paint removal formulation, an adhesive formulation, a latex paint formulation, or a coating formulation.

39. A plasticized polymer composition comprising
a) a base polymer, and
b) a plasticizer comprising one or more of the compounds:

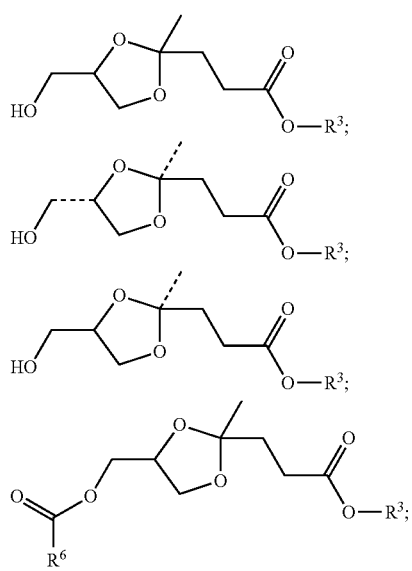

-continued

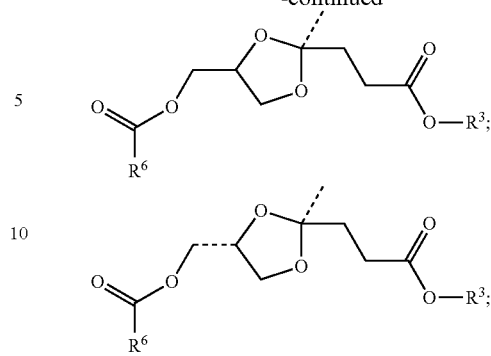

wherein
R³ is hydrogen; methyl; linear, branched or cyclic alkyl; linear, branched or cyclic alkenyl; aryl; aralkyl; or alkyloxyalkyl; and
R⁶ is hydrogen, methyl, linear, branched or cyclic alkyl; linear, branched or cyclic alkenyl; aryl; aralkyl; oxoalkyl; or alkyloxyalkyl.

40. The plasticized polymer composition of claim 39 wherein the one or more compounds are present at between 5 and 80% by weight of the composition.

41. The plasticized polymer composition of claim 39 wherein the one or more compounds are present at between 5 and 25% by weight of the composition.

42. The plasticized polymer composition of claim 39 further comprising one or more additional plasticizing compounds.

43. The plasticized polymer composition of claim 39 wherein the base polymer comprises poly(vinyl chloride) homopolymer or copolymer, a poly(3-hydroxyalkanoate) homopolymer or copolymer, poly(3-hydroxybutyrate), poly(lactate), or polysaccharide homopolymer or copolymer.

44. The plasticized polymer composition of claim 39 wherein R³ and R⁶ are linear or branched alkyl groups having between 1 and 23 carbons.

45. The plasticized polymer composition of claim 39 wherein R³ and R⁶ are linear or branched alkyl groups having between 1 and 12 carbons.

46. The plasticized polymer composition of claim 39 further comprising one or more additives comprising a stabilizer, an inorganic or organic filler, reinforcing fibers, pigments, and dyes.

47. The plasticized polymer composition of claim 39 wherein the composition is cast, molded, or extruded into a shape.

48. The plasticized polymer composition of claim 47 wherein the shape comprises film, fiber, tubing, or pipe.

49. A method of making a polymer comprising one or more repeat units having the structure:

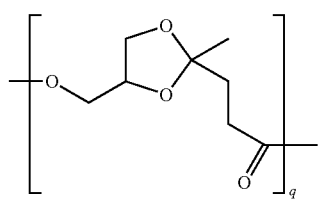

wherein q is an integer, the method comprising reacting one or more of the compounds:

[Structure: HOCH2-dioxolane(CH3)-CH2CH2-C(O)-O-R³]

[Structure: HO-CH2-dioxolane-CH2CH2-C(O)-O-R³; and]

[Structure: HO-CH2-dioxolane-CH2-C(O)-O-R³]

wherein R³ is hydrogen, methyl, linear, branched or cyclic alkyl, linear, branched or cyclic alkenyl, aryl, aralkyl, or alkyloxyalkyl;

in the presence of a polycondensation catalyst to form a polymer.

50. The method of claim 49 wherein the reaction is affected under conditions allowing for removal of R³OH by distillation.

51. The method of claim 49 wherein the polycondensation catalyst comprises an alkali metal, a transitional metal alkoxide, germanium oxide, an alkali metal alkoxide, sodium, an acid, an alkoxide of titanium, or tin (II) octanoate.

52. The method of claim 49 further comprising an inert solvent.

53. The method of claim 52 wherein the inert solvent comprises a hydrocarbon, a halogenated hydrocarbon, or an ether.

54. A method of making a polymer comprising one or more repeat units comprising:

[Polymer repeat unit structure with subscript q]

wherein q is an integer, the method comprising:

a) reacting a one or more of the compounds:

[Structure: R⁶-C(O)-O-CH2-dioxolane-CH2CH2-C(O)-O-R³]

[Structure: R⁶-C(O)-O-CH2-dioxolane-CH2CH2-C(O)-O-R³; and]

-continued

[Structure: R⁶-C(O)-O-CH2-dioxolane-CH2-C(O)-O-R³]

wherein

R³ is hydrogen, methyl, linear, branched or cyclic alkyl; linear, branched or cyclic alkenyl; aryl, aralkyl, or alkyloxyalkyl;

R⁶ is hydrogen, linear, branched or cyclic alkyl; linear, branched or cyclic alkenyl; aryl, aralkyl, oxoalkyl, or alkyloxyalkyl;

in the presence of a polycondensation catalyst to form the polymer.

55. The method of claim 54 wherein the reacting is effected under conditions allowing for removal of R⁶COOH by distillation.

56. The method of claim 54 wherein the polycondensation catalyst comprises an alkali metal, a transitional metal alkoxide, germanium oxide, an alkali metal alkoxide, sodium, an acid, an alkoxide of titanium, or tin (II) octanoate.

57. The method of claim 54 further comprising an inert solvent.

58. The method of claim 57 wherein the inert solvent comprises a hydrocarbon, a halogenated hydrocarbon, or an ether.

59. A method of making a polymer comprising one or more repeat units comprising:

[Polymer repeat unit structure with subscript q]

wherein p is an integer, the method comprising reacting a one or more of the compounds:

[Bicyclic structure]

[Macrocyclic dimer structure]

or a mixture thereof under ring opening polymerization conditions to form the polymer.

60. A method of making a compound of claim 2 comprising reacting a ketal compound having the formula:

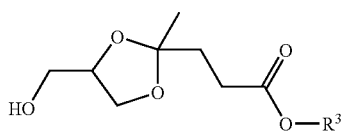

wherein
R³ is hydrogen; methyl; linear, branched or cyclic alkyl; linear, branched or cyclic alkenyl; aryl; aralkyl; or alkyloxyalkyl;
with a compound comprising an epoxide of either a normal α-olefin or an unsaturated fatty acid ester in the presence of an acid catalyst to form the compound.

61. The method of claim 60 wherein the epoxide of a normal α-olefin has the structure:

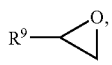

wherein R⁹ is a linear alkyl having 6 to 30 carbon atoms.

62. The method of claim 61 wherein R⁹ is a linear alkyl having 6 to 14 carbon atoms.

63. The method of claim 60 wherein R³ is not hydrogen.

64. The method of claim 60 wherein the acid catalyst comprises a strong mineral acid comprising sulfuric acid, hydrochloric acid, hydrofluoroboric acid, hydrobromic acid, p-toluenesulfonic acid, camphorosulfonic acid, methanesulfonic acid, or a resin comprising protonated sulfonic acid groups.

65. The method of claim 60 wherein the acid catalyst comprises a Lewis acid comprising BF₃ or a complex thereof, SnCl₂, SnCl₄, TiCl₄, AlCl₃, silica, acidic alumina, titania, zirconia, an acidic clay, a mixed aluminum oxide, or a mixed magnesium oxide.

66. The method of claim 60 wherein the acid catalyst comprises an activated carbon derivative comprising a mineral acid, sulfonic acid, or Lewis acid derivative.

67. The method of claim 60 wherein the reacting comprises elevating the temperature.

68. The method of claim 60 further comprising adding a cosolvent that is inert under the reaction conditions, and removing the cosolvent after the reacting.

69. The method of claim 60 wherein the cosolvent comprises a saturated hydrocarbon, an ether, or a polyether.

70. The method of claim 60 wherein the acid catalyst is neutralized or removed after the affecting of the reaction.

71. The method of claim 60 wherein the ketal is provided in a 2-20 molar excess over the epoxide of either a normal α-olefin or an unsaturated fatty acid ester.

72. The method of claim 60 further comprising saponifying the product of the reaction to the alkali or alkali-earth metal salt.

73. The method of claim 60 wherein the unsaturated fatty acid ester is a monohydric or polyhydric alcohol ester of a fatty acid, wherein the fatty acid is a linear monocarboxylic acid having from 10 to 24 carbon atoms and at least one double bond.

74. The method of claim 73 wherein the fatty acid has between one and three double bonds.

75. The method of claim 73 wherein the monohydric alcohol is a linear or branched primary or secondary alkanol or alkoxyalkanol having from 1 to 12 carbon atoms.

76. The method of claim 73 wherein the alkanol comprises methanol, ethanol, propanol, isopropanol, butanol, secondary butanol, isobutanol, isoamyl alcohol, or 2-ethylhexanol.

77. The method of claim 73 wherein the monohydric alcohol comprises an alkoxyalkanol comprising a primary or secondary alcohol having from 3 to 12 carbon atoms, and a linear, branched, or cyclic alkoxy group having from 1 to 8 carbon atoms is located in a vicinal position to the hydroxyl group of the alcohol.

78. The method of claim 73 wherein the monohydric alcohol comprises an alkoxyalkanol comprising tetrahydrofurfuryl alcohol.

79. The method of claim 73 wherein the polyhydric alcohol is a linear or branched polyhydroxylated alkane having from 1 to 6 hydroxyl groups.

80. The method of claim 73 wherein the polyhydric alcohol comprises ethylene glycol, propylene-1,2-diol, propane-1,3-diol, an isomer of butylenes glycol, glycerol, 1,2,4-trihydroxybutane, pentaerythritol, xylitol, ribitol, sorbitol, mannitol, or galactitol.

81. The method of claim 73 wherein the polyhydric alcohol comprises one or more ether bonds.

82. The method of claim 81 wherein the polyhydric alcohol comprises isosorbide, an isomer of sorbitan, or diglycerol.

83. The method of claim 73 wherein substantially all of the hydroxyl groups of the polyhydric alcohol are esterified with a fatty acid group.

84. The method of claim 83 further comprising a mixture of unsaturated and saturated fatty acid ester.

85. The method of claim 84 wherein the mixture is predominantly unsaturated fatty acid ester.

86. The method of claim 84 wherein the mixture comprises a triglyceride of a vegetable oil.

87. The method of claim 86 wherein the triglyceride of a vegetable oil comprises soybean oil, linseed oil, canola oil, safflower oil, sunflower oil, corn oil, castor oil, or a blend thereof.

88. The method of claim 84 wherein the fatty acid ester comprises a mixture comprising high oleic canola oil, an ester of 10-undecylenic acid, or a mixture of methyl esters of fatty acids derived from transesterification of a vegetable oil.

89. The method of claim 88 wherein the vegetable oil comprises soybean oil or canola oil.

90. The method of claim 60 wherein the epoxide an unsaturated fatty acid ester comprises a mixture of an unsaturated fatty acid ester and one or more saturated fatty acid esters.

91. The method of claim 60 wherein the unsaturated fatty acid ester is partially hydrogenated.

92. The method of claim 60 wherein the unsaturated fatty acid ester is isomerized to change position or stereochemistry of the double bonds.

93. The method of claim 60 wherein the epoxide of an unsaturated fatty acid ester comprises at least one epoxidized double bond.

94. The method of claim 93 wherein the epoxidized unsaturated fatty acid ester comprises a majority of epoxidized double bonds.

95. A surfactant comprising an alkali metal salt, an alkali-earth metal salt, amine salt, or ammonium salt of one or more of the compounds:

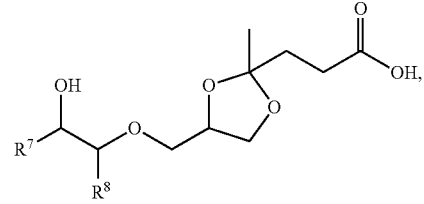

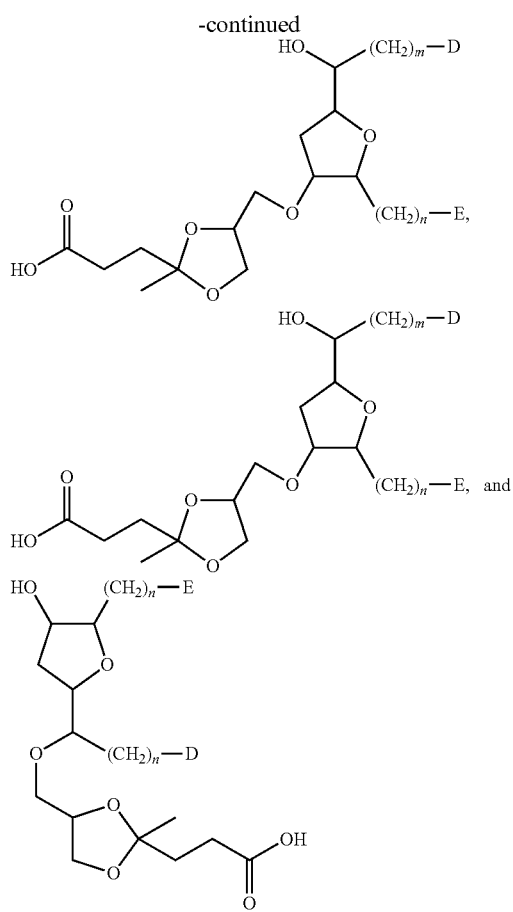

wherein one of $R^7$ or $R^8$ is hydrogen and the other is a $C_1$-$C_{30}$ linear alkyl; one of E or D is hydrogen and the other is carboxyl; and m and n are independently integers from 0 to 20, such that the sum of m+n=8 to 21.

96. A composition comprising the surfactant of claim 95.

97. The composition of claim 96 further comprising one or more additional surfactants, solvents, glycols, polyols, fragrances, colors, biologically active additives, inert additives, enzymes, or wetting agents.

98. The composition of claim 96 wherein the composition is a cleaning composition, dishwashing composition, laundry washing composition, cosmetics composition, personal care composition, or degreasing composition.

99. The composition of claim 96 wherein the surfactant is present in a concentration of at least 0.001% of the composition.

100. A surfactant comprising an amide of one or more of the compounds: wherein

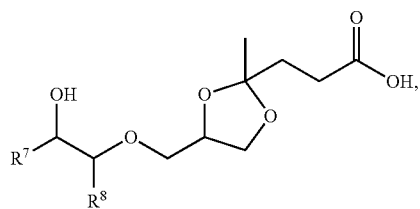

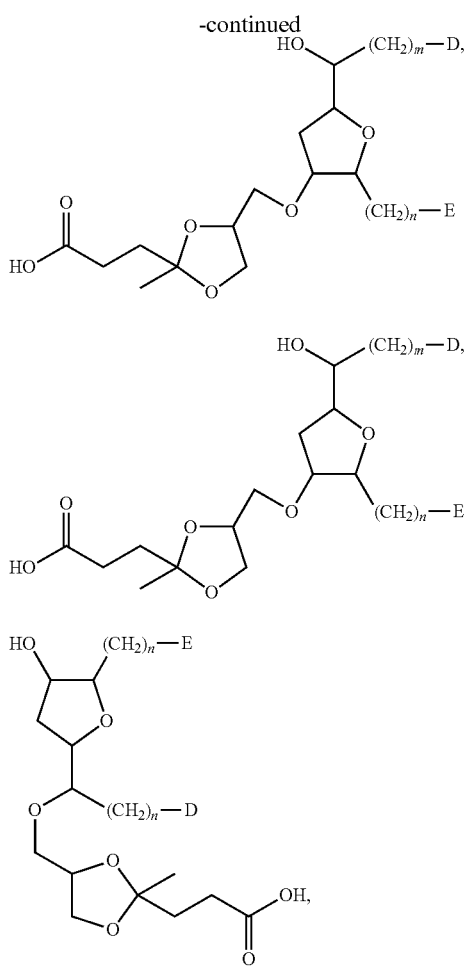

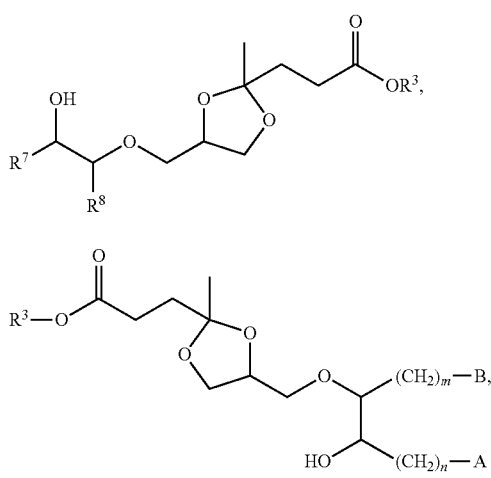

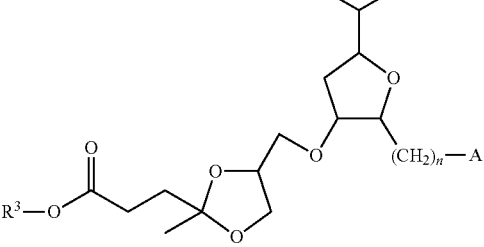

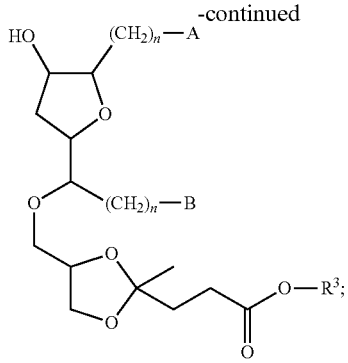

R³ is hydrogen; methyl; linear, branched or cyclic alkyl; linear, branched or cyclic alkenyl; aryl; aralkyl or alkyloxyalkyl;

one of R⁷ or R⁸ is hydrogen and the other is a $C_1$-$C_{30}$ linear alkyl;

one of A or B is hydrogen and the other is an ester;

m and n are independently integers from 0 to 20, such that the sum of m+n=8 to 21; and one of E or D is hydrogen and the other is carboxyl.

101. The surfactant of claim 100 wherein the amide is an amide of a primary or secondary alkylamine or an aminoalcohol.

102. A composition comprising the surfactant of claim 100.

103. The composition of claim 102 further comprising one or more additional surfactant, solvent, glycol, polyol, fragrance, color, biologically active additive, inert additive, enzyme, or wetting agent.

104. The composition of claim 102 wherein the composition comprises a cleaning composition, dishwashing composition, laundry washing composition, cosmetics composition, personal care composition, or degreasing composition.

105. The composition of claim 102 wherein the surfactant is present in a concentration of at least 0.001% of the composition.

106. A plasticized polymer composition comprising:
a) a base polymer; and
b) a compound of claim 2.

107. The plasticized polymer composition of claim 106, wherein the base polymer comprises vinyl chloride polymer, poly(3-hydroxyalkanoate) polymer, poly(lactate) polymer, or polysaccharide polymer.

108. A plasticized polymer composition comprising
a) a base polymer; and
b) a compound of claim 20.

109. The plasticized polymer composition of claim 108, wherein the base polymer comprises vinyl chloride polymer, poly(3-hydroxyalkanoate) polymer, poly(lactate) polymer, or polysaccharide polymer.

110. A method of using a ketal compound to manufacture a formulation, the method comprising:
combining the ketal compound with a base formulation, wherein the ketal compound is one or more of the compounds:

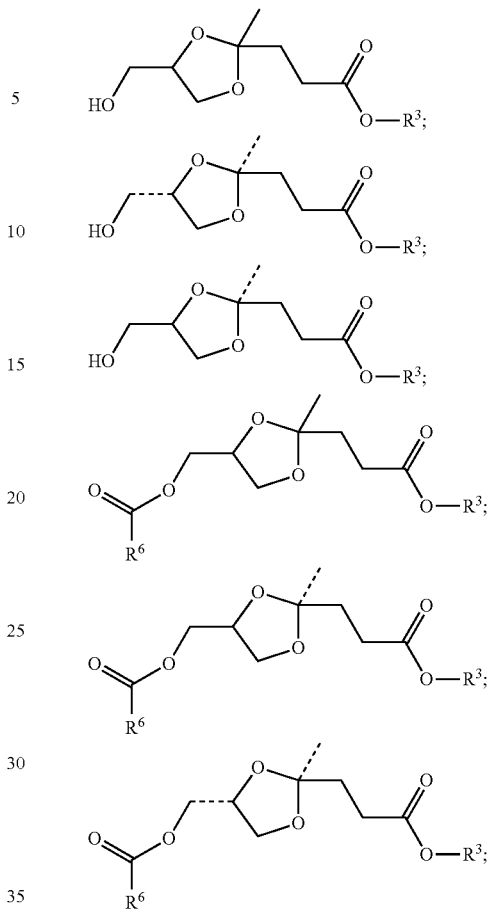

wherein
R³ is hydrogen; methyl; linear, branched or cyclic alkyl; linear, branched or cyclic alkenyl; aryl; aralkyl; or alkyloxyalkyl; and
R⁶ is hydrogen; methyl; linear, branched or cyclic alkyl; linear, branched or cyclic alkenyl; aryl; aralkyl; oxoalkyl; or alkyloxyalkyl, or a salt thereof.

111. The method of claim 110, wherein the formulation is a degreasing formulation.

112. The method of claim 110, wherein the formulation is a paint thinning formulation.

113. The method of claim 110, wherein the formulation is a paint removal formulation.

114. The method of claim 110, wherein the formulation is an adhesive formulation.

115. The method of claim 110, wherein the formulation is a latex paint formulation.

116. The method of claim 110, wherein the formulation is a coating formulation.

117. The formulation of claim 37, comprising
a degreasing formulation; and
one or more of the compounds:

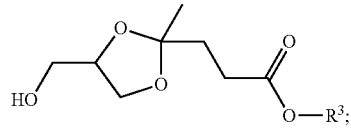

-continued

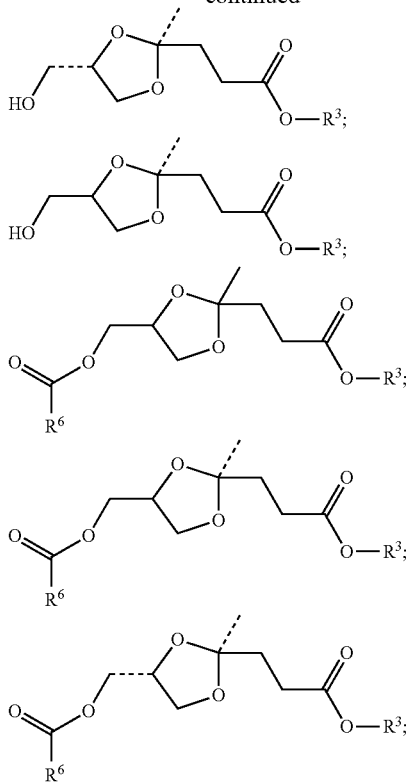

wherein
R³ is hydrogen; methyl; linear, branched or cyclic alkyl; linear, branched or cyclic alkenyl; aryl; aralkyl; or alkyloxyalkyl; and
R⁶ is hydrogen; methyl; linear, branched or cyclic alkyl; linear, branched or cyclic alkenyl; aryl; aralkyl; oxoalkyl; or alkyloxyalkyl, or a salt thereof.

118. The formulation of claim 37, comprising
a paint thinning formulation; and
one or more of the compounds:

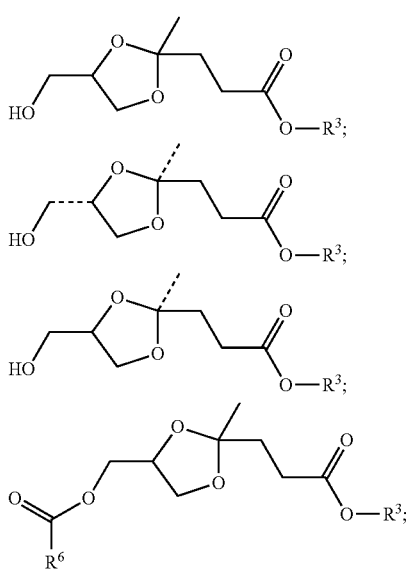

-continued

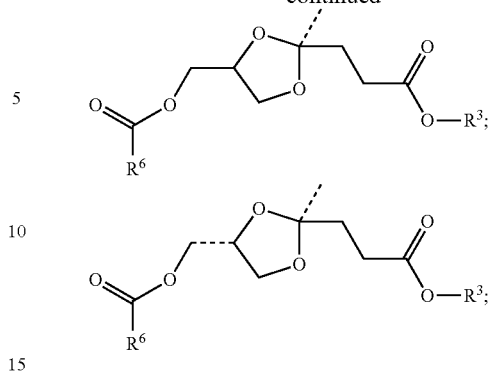

wherein
R³ is hydrogen; methyl; linear, branched or cyclic alkyl; linear, branched or cyclic alkenyl; aryl; aralkyl; or alkyloxyalkyl; and
R⁶ is hydrogen; methyl; linear, branched or cyclic alkyl; linear, branched or cyclic alkenyl; aryl; aralkyl; oxoalkyl; or alkyloxyalkyl, or a salt thereof.

119. The formulation of claim 37, comprising
a paint removal formulation; and
one or more of the compounds:

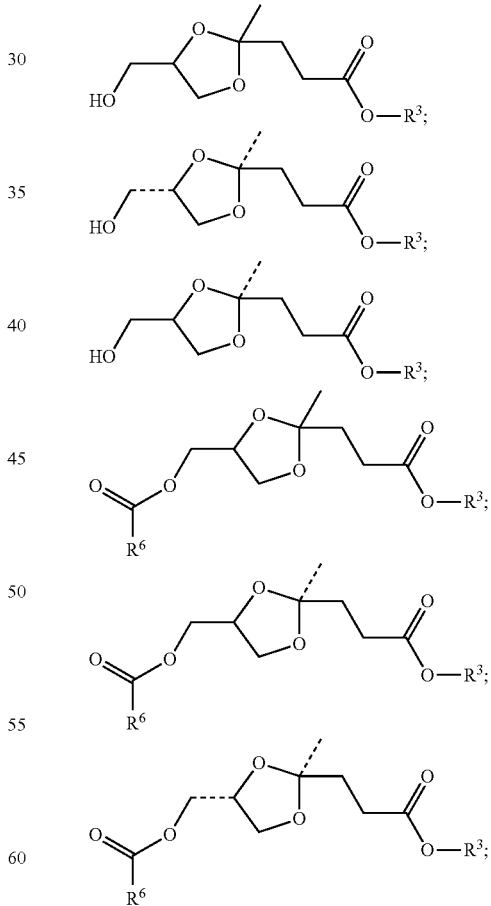

wherein
R³ is hydrogen; methyl; linear, branched or cyclic alkyl; linear, branched or cyclic alkenyl; aryl; aralkyl; or alkyloxyalkyl; and R⁶ is hydrogen; methyl; linear, branched or cyclic alkyl; linear, branched or cyclic alkenyl; aryl; aralkyl; oxoalkyl; or alkyloxyalkyl, or a salt thereof.

120. The formulation of claim 37, comprising
an adhesive formulation; and
one or more of the compounds:

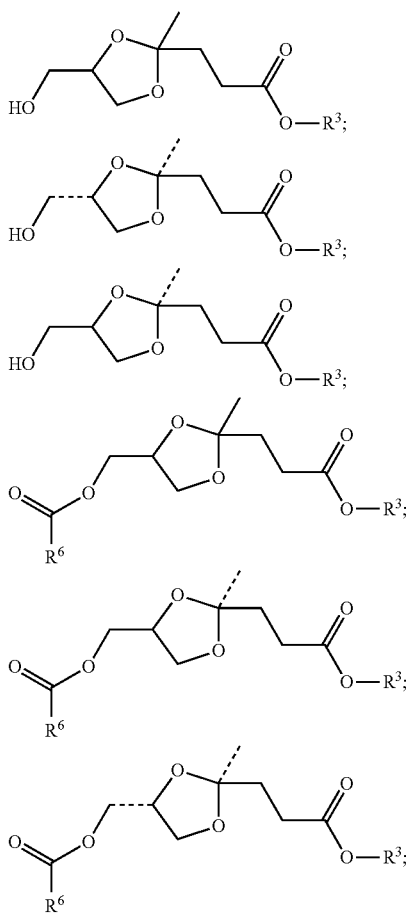

wherein
R³ is hydrogen; methyl; linear, branched or cyclic alkyl; linear, branched or cyclic alkenyl; aryl; aralkyl; or alkyloxyalkyl; and
R⁶ is hydrogen; methyl; linear, branched or cyclic alkyl; linear, branched or cyclic alkenyl; aryl; aralkyl; oxoalkyl; or alkyloxyalkyl, or a salt thereof.

121. The formulation of claim 37, comprising
a latex paint formulation; and
one or more of the compounds:

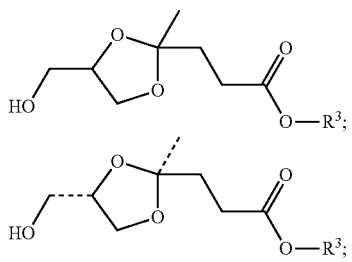

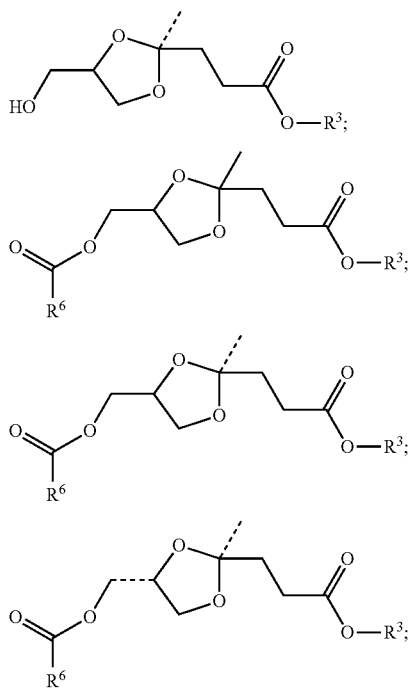

wherein
R³ is hydrogen; methyl; linear, branched or cyclic alkyl; linear, branched or cyclic alkenyl; aryl; aralkyl; or alkyloxyalkyl; and
R⁶ is hydrogen; methyl; linear, branched or cyclic alkyl; linear, branched or cyclic alkenyl; aryl; aralkyl; oxoalkyl; or alkyloxyalkyl, or a salt thereof.

122. The formulation of claim 37, comprising
a coating formulation; and
one or more of the compounds:

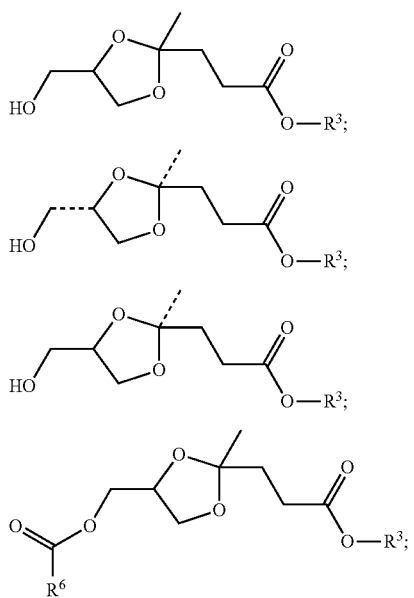

-continued

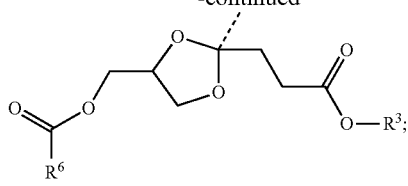

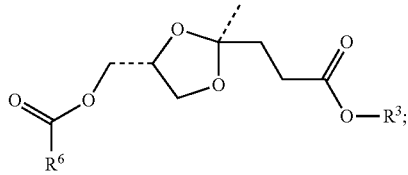

wherein $R^3$ is hydrogen; methyl; linear, branched or cyclic alkyl; linear, branched or cyclic alkenyl; aryl; aralkyl; or alkyloxyalkyl; and $R^6$ is hydrogen; methyl; linear, branched or cyclic alkyl; linear, branched or cyclic alkenyl; aryl; aralkyl; oxoalkyl; or alkyloxyalkyl, or a salt thereof.

123. The method of claim 18, wherein p is between 1 and 10.

124. The method of claim 19, wherein p is between 1 and 10.

125. The compound of claim 29, wherein p is between 1 and 10.

126. The compound of claim 1, wherein X is

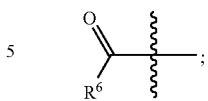

wherein $R^6$ is selected from hydrogen; linear, branched, or cyclic alkyl; linear, branched or cyclic alkenyl; aryl; aralkyl; oxoalkyl; and alkyloxyalkyl.

127. The compound of claim 126, wherein $R^3$ and $R^6$ is each a linear or branched $C_1$-$C_{12}$ alkyl.

128. The compound of claim 33, wherein $R^9$ is hydrogen and $R^{10}$ is $OR^{11}$, wherein $R^{11}$ is hydrogen, methyl, or a linear, branched, or cyclic alkyl.

129. The compound of claim 33, having the formula

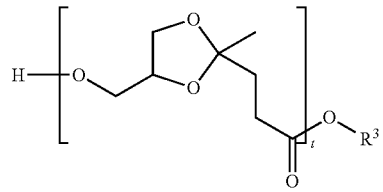

wherein $R^3$ is methyl, or a linear, branched, or cyclic alkyl, and t is an integer of 2-4.

130. The compound of claim 129, wherein $R^3$ is n-butyl.

131. The method of claim 19, the method further comprising separation of the products by distillation.

* * * * *

UNITED STATES PATENT AND TRADEMARK OFFICE
CERTIFICATE OF CORRECTION

| | | |
|---|---|---|
| PATENT NO. | : 8,053,468 B2 | Page 1 of 1 |
| APPLICATION NO. | : 11/915549 | |
| DATED | : November 8, 2011 | |
| INVENTOR(S) | : Sergey Selifonov | |

It is certified that error appears in the above-identified patent and that said Letters Patent is hereby corrected as shown below:

Column 41, lines 48-55, please change the formula

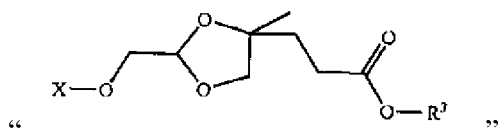

" "

to

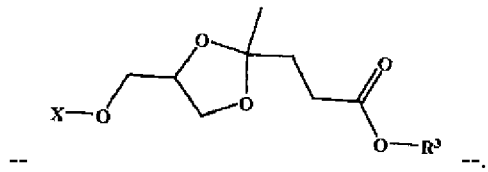

-- --.

Signed and Sealed this
Sixth Day of March, 2012

David J. Kappos
*Director of the United States Patent and Trademark Office*